(12) United States Patent
Zhang et al.

(10) Patent No.: US 7,196,083 B2
(45) Date of Patent: *Mar. 27, 2007

(54) HETEROPOLYCYCLIC INHIBITORS OF PROTEIN KINASES

(75) Inventors: Zaihui Zhang, Richmond (CA); Xinyao Du, Richmond (CA); Serguei Sviridov, Burnaby (CA); Greg Chopiuk, Vancouver (CA)

(73) Assignee: OLT Inc., Vancouver (CA)

( * ) Notice: Subject to any disclaimer, the term of this patent is extended or adjusted under 35 U.S.C. 154(b) by 197 days.

This patent is subject to a terminal disclaimer.

(21) Appl. No.: 10/310,600

(22) Filed: Dec. 4, 2002

(65) Prior Publication Data

US 2003/0144294 A1    Jul. 31, 2003

Related U.S. Application Data

(63) Continuation of application No. 09/900,073, filed on Jul. 6, 2001, now Pat. No. 6,514,972, which is a continuation-in-part of application No. 09/611,038, filed on Jul. 6, 2000, now abandoned.

(51) Int. Cl.
*A61K 31/53* (2006.01)
(52) U.S. Cl. .................................... 514/243
(58) Field of Classification Search ............... 514/243
See application file for complete search history.

(56) References Cited

U.S. PATENT DOCUMENTS

| 5,221,627 | A |   | 6/1993 | Grigg et al. |   |
|---|---|---|---|---|---|
| 5,789,427 | A |   | 8/1998 | Chen et al. |   |
| 6,514,972 | B2 | * | 2/2003 | Zhang et al. | 514/243 |

FOREIGN PATENT DOCUMENTS

WO            01/79209    * 10/2001

OTHER PUBLICATIONS

Kane et al. (1999), "Induction of NF-κB by the Akt/PKB Kinase," *Current Biology*, vol. 9:601-604.
Junek et al., *Syntheses with nitriles XLV 2- (1, 3-Dioxo-2-indanylidene) benzimidazoline-and isomer of indigo*, Inst. Org. Chem., 1977, 2276-82, 110(6), Univ. Graz, Graz, Austria.

* cited by examiner

*Primary Examiner*—Phyllis G. Spivack
(74) *Attorney, Agent, or Firm*—Pamela J. Sherwood; Bozicevic, Field & Francis LLP

(57) ABSTRACT

A method of inhibiting tumor growth is provided, comprising administering an effective dose of a compound of the formula

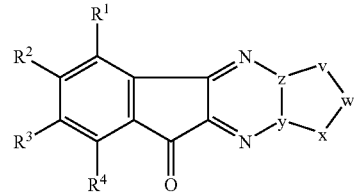

wherein, independently at each occurrence, w is C or N, v and x are N with H substitution as needed to fulfill open valence sites;

y and z are selected from N and C, with H substitution as needed to fulfill open valence sites, with the proviso that each of w, v, x, y and z is not simultaneously C;

the ring formed from v, w, x, y and z may be saturated or unsaturated; and $R^1$, $R^2$, $R^3$ and $R^4$ are selected from hydrogen, alkyl, aryl, alkaryl, aralkyl, heteroalkyl, and heteroaryl; wherein any adjacent two of $R^1$, $R^2$, $R^3$ and $R^4$ may join together to form a 5, 6 or 7-membered carbocyclic ring or a 5, 6 or 7-membered heterocyclic ring containing at least one atom selected from nitrogen, oxygen and sulfur.

12 Claims, 5 Drawing Sheets

HETEROPOLYCYCLIC INHIBITORS OF PROTEIN KINASES

BACKGROUND OF THE INVENTION

Protein phosphorylation is a fundamental process for the regulation of cellular functions. The coordinated action of both protein kinases and phosphatases controls the levels of phosphorylation and, hence, the activity of specific target proteins. One of the predominant roles of protein phosphorylation is in signal transduction, where extracellular signals are amplified and propagated by a cascade of protein phosphorylation and dephosphorylation events.

While a plethora of extracellular molecules exist that modulate cellular functions via binding to membrane receptors inside the cell, their actions are mediated by relatively few signaling mechanisms within the cell. One of these mechanisms is activation of phosphatidylinositol 3-kinase (PI-3K), which results in the generation of membrane-restricted second messenger polyphosphatidyl-inositides containing a 3'-phosphate, and the activation of protein kinase B (PKB). Activated PKB induces NF-κB (Kane et al. (1999) Curr Biol 1999 June 3;9(11):601–4); mediates a number of metabolic effects of insulin; and protects cells from apoptosis.

Most proliferating cells are programmed to undergo apoptosis unless specific survival signals are provided. Survival factors can suppress apoptosis in a transcription-independent manner by activating the serine/threonine kinase PKB, which then phosphorylates and inactivates components of the apoptotic machinery. Survival factor withdrawal triggers apoptosis by inducing the expression of genes that are critical for cell death.

Signal transduction also plays a key regulatory role in the growth and metastatic potential of tumor cells. These signaling pathways form an interconnecting grid that serves to regulate the homeostatic, survival and invasive functions of the cell. Among the key regulatory molecules in these pathways are the serine/threonine-protein kinases cyclic AMP-dependent protein kinase (PKA), Akt (PKB) and protein kinase C (PKC). These protein kinases modulate pathways associated with tumor proliferation, cell survival and multidrug resistance, and at a molecule level are likely to serve as effective targets for drug design.

SUMMARY OF THE INVENTION

Pharmaceutical compositions and compounds are provided. The compounds of the invention are heteropolycyclic compounds. In one embodiment of the invention, formulations of the compounds in combination with a physiologically acceptable carrier are provided. The pharmaceutical formulations are useful in the treatment of disorders associated with hyperproliferation, and responses to insulin signaling. The compounds are also active in the inhibition of specific protein kinases.

DETAILED DESCRIPTION OF THE INVENTION

Figure 1:
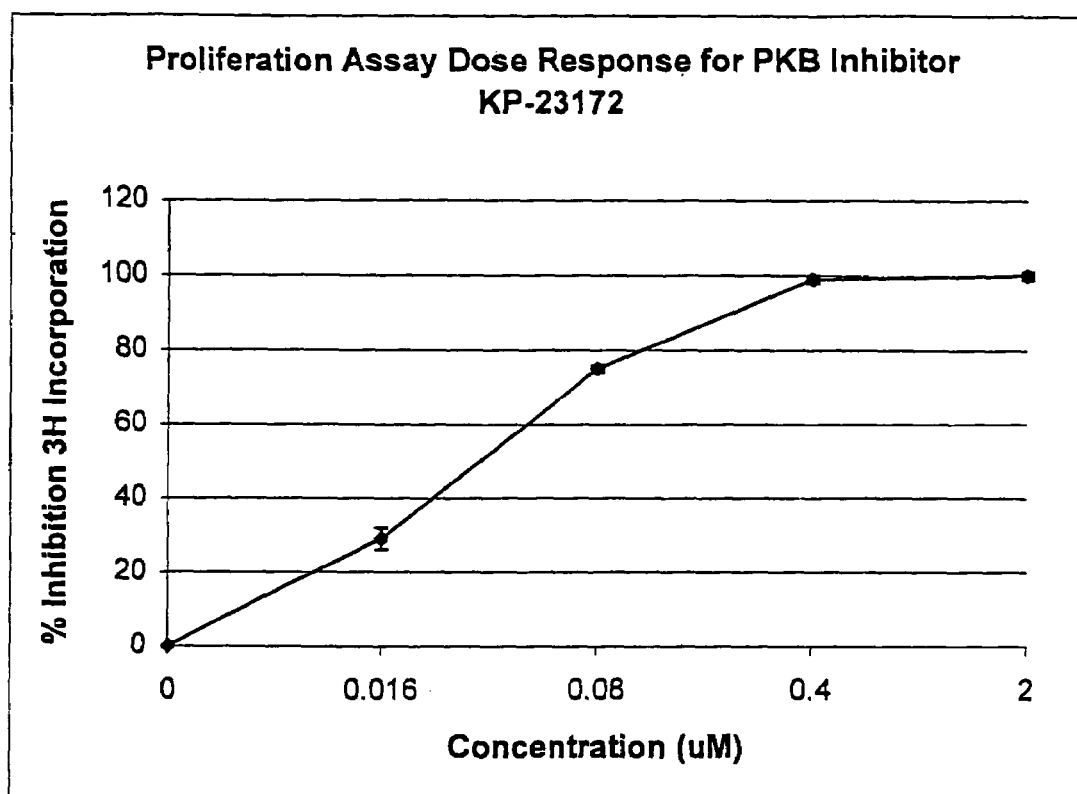
FIG. 1 graphically shows the effect of KP-23172 on U87 proliferation (thymidine incorporation). Compounds were added to culture at mid-logarithmic growth and incubated for 20 hours. (N=8 for the values+standard errors). $IC_{50}$ value was calculated to be 50 nM.

The present invention provides novel heteropolycyclic fused ring compounds, compositions and methods as set forth within this specification. In general, all technical and scientific terms used herein have the same meaning as commonly understood to one of ordinary skill in the art to which this invention belongs, unless clearly indicated otherwise. For clarification, listed below are definitions for certain terms used herein to describe the present invention. These definitions apply to the terms as they are used throughout this specification, unless otherwise clearly indicated.

Definition of Terms

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

"Acyl" is a specie of heteroalkyl wherein a terminal carbon of the heteroalkyl group is in the form of a carbonyl group, i.e., (alkyl or heteroalkyl)-C=O, where examples include acetyl ($CH_3$—(C=O)—).

"Acyloxy" refers to a heteroalkylene group of the formula —C(=O)—O— bonded to "X" so as to form —C(=O)—O—X wherein X may be any of alkyl, aryl, heteroalkyl, or heteroaryl.

"Alkenyl" is a specie of alkyl group, where an alkenyl group has at least one carbon—carbon double bond.

"Alkenylene" is a specie of alkylene group where the alkylene group has at least one double bond.

"Alkyl" is a monovalent, saturated or unsaturated, straight, branched or cyclic, aliphatic (i.e., not aromatic) hydrocarbon group. In various embodiments, the alkyl group has 1–20 carbon atoms, i.e., is a C1–C20 (or $C_1$–$C_{20}$) group, or is a C1–C18 group, a C1–C12 group, a C1–C6 group, or a C1–C4 group. Independently, in various embodiments, the alkyl group: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$alkyl (i.e., —$CH_3$ (methyl)), $C_2$alkyl (i.e., —$CH_2CH_3$ (ethyl), —CH=$CH_2$ (ethenyl) and —C≡CH (ethynyl)) and $C_3$alkyl (i.e., —$CH_2CH_2CH_3$ (n-propyl), —CH($CH_3$)$_2$ (i-propyl), —CH=CH—$CH_3$ (1-propenyl), —C≡C—$CH_3$ (1-propynyl), —$CH_2$—CH=$CH_2$ (2-propenyl), —$CH_2$—C≡CH (2-propynyl), —C($CH_3$)=$CH_2$ (1-methylethenyl), and —CH($CH_2$)$_2$ (cyclopropyl)).

"Alkylene" is a polyvalent, saturated or unsaturated, straight, branched or cyclic, aliphatic (i.e., not aromatic)

hydrocarbon group. In various embodiments, the alkylene group has 1–20 carbon atoms, i.e., is a C1–C20 group, or is a C1–C18 group, a C1–C12 group, a C1–C6 group, or a C1–C4 group. Independently, in various embodiments, the alkylene group: has zero branches (i.e., is a straight chain), one branch, two branches, or more than two branches; is saturated; is unsaturated (where an unsaturated alkylene group may have one double bond, two double bonds, more than two double bonds, and/or one triple bond, two triple bonds, or more than three triple bonds); is or contains a cyclic group; is acyclic; is divalent, i.e., has two open sites that each bond to a non-alkylene group; is trivalent, i.e., has three open sites that each bond to a non-alkylene group; has more than three open sites. Exemplary alkylene groups include $C_1$alkylene (i.e., —$CH_2$—) and $C_2$alkylene (i.e., —$CH_2CH_2$—, —CH═CH—, —C C—, —C(═$CH_2$)—, and —CH($CH_3$)—).

"Aralkenyl" is another name for arylalkenylene, wherein at least one of the open bonding sites of an alkenylene group is bonded to an aryl group.

"Aralkyl" is another name for arylalkylene, wherein at least one of the open bonding sites of an alkylene group is bonded to an aryl group, where benzyl is an example.

"Aryl" is a monovalent, aromatic, hydrocarbon, ring system. The ring system may be monocyclic or fused polycyclic (e.g., bicyclic, tricyclic, etc.). In various embodiments, the monocyclic aryl ring is C5–C10, or C5–C7, or C5–C6, where these carbon numbers refer to the number of carbon atoms that form the ring system. A C6 ring system, i.e., a phenyl ring, is a preferred aryl group. In various embodiments, the polycyclic ring is a bicyclic aryl group, where preferred bicyclic aryl groups are C8–C12, or C9–C10. A naphthyl ring, which has 10 carbon atoms, is a preferred polycyclic aryl group.

"Arylene" is a polyvalent, aromatic hydrocarbon, ring system. The ring system may be monocyclic or fused polycyclic (e.g., bicyclic, tricyclic, etc.). In various embodiments, the monocyclic arylene group is C5–C10, or C5–C7, or C5–C6, where these carbon numbers refer to the number of carbon atoms that form the ring system. A C6 ring system, i.e., a phenylene ring, is a preferred aryl group. In various embodiments, the polycyclic ring is a bicyclic arylene group, where preferred bicyclic arylene groups are C8–C12, or C9–C10. A naphthylene ring, which has 10 carbon atoms, is a preferred polycyclic aryl group. The arylene group may be divalent, i.e., it has two open sites that each bond to another group; or trivalent, i.e., it has three open sites that each bond to another group; or it may have more than three open sites.

"Cycloalkenyl" is a specie of alkyl group where a cycloalkenyl group is a cyclic hydrocarbon group with at least one double bond.

"Cycloalkenylene" is a specie of alkylene group which is a cyclic hydrocarbon with at least one double bond and with at least two bonding sites.

"Cycloalkyl" is a specie of alkyl group, where a cycloalkyl is a cyclic hydrocarbon group.

"Cycloalkylalkylene" is a species of alkyl group wherein at least one open bonding site of an alkylene group is joined to a cycloalkyl group.

"Cycloalkylene" is a specie of alkylene group which is a cyclic hydrocarbon group with at least two open bonding sites.

"Cycloalkylenealkylene" is a specie of alkylene group wherein a cycloalkylene group is bonded to a non-cyclic alkylene group, and each of the cycloalkylene and non-cyclic alkylene group have at least one open bonding site.

Haloalkyl is a specie of heteroalkyl wherein at least one carbon of an alkyl group is bonded to at least one halogen.

"Halogen" refers to fluorine, chlorine, bromine and iodide. Fluorine and chlorine are preferred halogens in compounds and compositions of the present invention.

Heteroalkylenearyl is a heteroalkylene group with at least one of its open bonding sites joined to an aryl group, where benzoyl (—C(═O)—Ph) is an example.

"Heteroalkyl" is an alkyl group (as defined herein) wherein at least one of the carbon atoms is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted.

"Heteroalkylene" is an alkylene group (as defined herein) wherein at least one of the carbon atoms is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom.

"Heteroaralkenyl" is another name for heteroarylalkenylene, wherein at least one of the open bonding sites of an alkenylene group is bonded to a heteroaryl group.

"Heteroaralkyl" is another name for heteroarylalkylene, wherein at least one of the open bonding sites of an alkylene group is bonded to a heteroalkyl group.

"Heteroaryl" is a monovalent aromatic ring system containing carbon and at least one heteroatom in the ring. The heteroaryl group may, in various embodiments, have one heteroatom, or 1–2 heteroatoms, or 1–3 heteroatoms, or 1–4 heteroatoms in the ring. Heteroaryl rings may be monocyclic or polycyclic, where the polycyclic ring may contained fused, spiro or bridged ring junctions. In one embodiment, the heteroaryl is selected from monocyclic and bicyclic. Monocyclic heteroaryl rings may contain from about 5 to about 10 member atoms (carbon and heteroatoms), preferably from 5–7, and most preferably from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. Exemplary heteroaryl groups include benzofuran, benzothiophene, furan, imidazole, indole, isothiazole, oxazole, piperazine, pyrazine, pyrazole, pyridazine, pyridine, pyrimidine, pyrrole, quinoline, thiazole and thiophene.

"Heteroarylene" is a polyvalent aromatic ring system containing carbon and at least one heteroatom in the ring. In other words, a heteroarylene group is a heteroaryl group that has more than one open site for bonding to other groups. The heteroarylene group may, in various embodiments, have one heteroatom, or 1–2 heteroatoms, or 1–3 heteroatoms, or 1–4 heteroatoms in the ring. Heteroarylene rings may be monocyclic or polycyclic, where the polycyclic ring may contained fused, spiro or bridged ring junctions. In one embodiment, the heteroaryl is selected from monocyclic and bicyclic. Monocyclic heteroarylene rings may contain from about 5 to about 10 member atoms (carbon and heteroatoms), preferably from 5–7, and most preferably from 5–6 member atoms in the ring. Bicyclic heteroarylene rings may contain from about 8–12 member atoms, or 9–10 member atoms in the ring.

"Heteroatom" is a halogen, nitrogen, oxygen, silicon or sulfur atom. Groups containing more than one heteroatom may contain different heteroatoms.

Salts of compounds of the present invention are preferably pharmaceutically acceptable salts, and are preferably acid addition salts.

"Pharmaceutically acceptable salt" and "salts thereof" in the compounds of the present invention refers to acid addition salts and base addition salts.

Acid addition salts refer to those salts formed from compounds of the present invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts refer to those salts formed from compounds of the present invention and inorganic bases such as sodium, potassium, lithium, ammonium, calcium, magnesium, iron, zinc, copper, manganese, aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

In one aspect, the present invention provides compounds having the structure

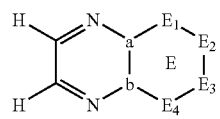

and salts thereof wherein, independently at each occurrence,
a and b are selected from C, S, O and N, provided that at least one of a and b is C;
  the E ring may be saturated or unsaturated;
  $E_1$, $E_2$ and $E_3$ are selected from C, S, O and N;
  $E_4$ is C, N, or a direct bond;
  providing that in each instance where $E_1$, $E_2$, $E_3$, or $E_4$ may be substituted with hydrogen, then that hydrogen may be replaced with a group selected from $R^1$, $R^2$, and $R^3$, and each of the two hydrogen shown in the structure may be replaced with a group selected from $R^1$, $R^2$, and $R^3$, where $R^1$ is selected from alkyl, heteroalkyl, aryl and heteroaryl; $R^2$ is selected from $(R^1)_n$-alkylene, $(R^1)_n$-heteroalkylene, $(R^1)_n$-arylene and $(R^1)_n$-heteroarylene; $R^3$ is selected from $(R^2)_n$-alkylene, $(R^2)_n$-heteroalkylene, $(R^2)_n$-arylene, and $(R^2)_n$-heteroarylene; and n is selected from 0, 1, 2, 3, 4 and 5;

further providing that any two adjacent $E_1$, $E_2$, $E_3$, $E_4$ may, with 3 or 4 additional carbons, form a five- or six-membered fused ring respectively, where the fused ring may be saturated or unsaturated;

and further providing that the two hydrogens shown in the structure may be replaced with a five- or six-membered fused ring structure;

where a fused ring structure may be substituted with 0, 1 or 2 groups selected from $R^1$, $R^2$ and $R^3$.

In another aspect, the present invention provides compounds having the structure

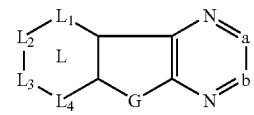

and salts thereof wherein, independently at each occurrence,
  G is selected from $CH_2$, C=O, NH, C=N—$NH_2$ and C=N—N(H)($R^1$);
  a and b are selected from CH, C—$R^1$, C—$R^2$ and C—$R^3$;
  the L ring may be saturated or unsaturated;
  $L_1$, $L_2$, $L_3$ and $L_4$ each represent C, with the proviso that $L_3$ and $L_4$ are fused to a five- or six-membered ring, and $L_1$+$L_2$ and $L_2$+$L_3$ may likewise be fused to a five- or six-membered ring, where a fused ring may be saturated or unsaturated, and where a fused ring may be substituted with 1, 2 or 3 substituents selected from $R^1$, $R^2$ and $R^3$;
  providing that in each instance where $L_1$, $L_2$, $L_3$ and $L_4$ may be substituted with hydrogen, then that hydrogen may be replaced with a group selected from $R^1$, $R^2$, and $R^3$;
  where $R^1$ is selected from alkyl, heteroalkyl, aryl and heteroaryl; $R^2$ is selected from $(R^1)_n$-alkylene, $(R^1)_n$-heteroalkylene, $(R^1)_n$-arylene and $(R^1)_n$-heteroarylene; $R^3$ is selected from $(R^2)_n$-alkylene, $(R^2)_n$-heteroalkylene, $(R^2)_n$-arylene, and $(R^2)_n$-heteroarylene; and n is selected from 0, 1, 2, 3, 4 and 5.

In another aspect, the present invention provides compounds of the formula

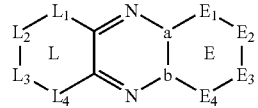

and salts thereof wherein, independently at each occurrence,
  a and b are selected from C, S, O and N, provided that at least one of a and b is C;
  the L and E rings may be saturated or unsaturated;
  $E_1$, $E_2$ and $E_3$ are selected from C, S, O and N;
  $E_4$ is C, N, or a direct bond;
  $L_1$, $L_2$ and $L_3$ each represent C;
  $L_4$ is C or a direct bond;
  providing that in each instance where $E_1$, $E_2$, $E_3$, $E_4$, $L_1$, $L_2$, $L_3$ and $L_4$ may be substituted with hydrogen, then that hydrogen may be replaced with a group selected from $R^1$, $R^2$, and $R^3$, where $R^1$ is selected from alkyl, heteroalkyl, aryl and heteroaryl; $R^2$ is selected from $(R^1)_n$-alkylene, $(R^1)_n$-heteroalkylene, $(R^1)_n$-arylene and $(R^1)_n$-heteroarylene; $R^3$ is selected from $(R^2)_n$-alkylene, $(R^2)_n$-heteroalkylene, $(R^2)_n$-arylene, and $(R^2)_n$-heteroarylene; and n is selected from 0, 1, 2, 3, 4 and 5; further providing that any two adjacent $E_1$, $E_2$, $E_3$, $E_4$ $L_1$, $L_2$, $L_3$ and $L_4$ may, with 3 or 4 additional carbons, form a five- or six-membered fused ring respectively, where the fused ring may be saturated or unsaturated;

and further providing that at least one five- or six-membered ring is fused to $E_1$ and $E_2$; $E_2$ and $E_3$; $E_3$ and $E_4$; $L_1$ and $L_2$; $L_2$ and $L_3$; and $L_3$ and $L_4$.

present in the compounds of the invention being located at the top and at the bottom of the structure. Likewise, a 5l-6c-6r ring system has a 6-membered central ring (6c) with a 5-membered ring fused to the left (5l) and a six-membered ring fused to the right (6r). Finally, a 6l-6c-6r ring system has a 6-membered central ring (6c) with a 6-membered ring fused to the left (6l) and a six-membered ring fused to the right (6r).

The structures shown in Table A show the basic (5l/6l)-6c-(5r/6r) structures as well as exemplary unsaturation that may be present within these three fused ring systems.

TABLE A

Thus, in various aspects and embodiments, the present invention provides compounds that include, i.e., comprise, the structures shown in Table A. In Table A, the structures are found within columns having headings 5l-6c-5r, 5l-6c-6r or 6l-6c-6r. This nomenclature is explained as follows. A 5l-6c-5r ring system has a 6-membered central ring (6c) with a 5-membered ring fused to the left (5l) and a five-membered ring fused to the right (5r). Left and right are defined relative to one another, with the two nitrogen atoms necessarily Compounds of the present invention include at least four fused rings. As explained above, three of those rings are in one of the 5l-6c-5r, 5l-6c-6r or 6l-6c-6r arrangements. The necessary fourth fused ring is fused to 5l, 6l, 5r, and/or 6r, but not to 6c. Thus a 5l or 5r ring has two possible fusion sites, while 6l and 6r have three possible fusion sites. The fourth fused ring is either a five-membered ring or a six-membered ring. These options are set forth in Tables B(1 and 2) and C(1 and 2) below. In Tables B and C, the 6r and r5 rings are shown composed entirely of carbon (Tables B1 and C1) or composed of one nitrogen with the remaining atoms being carbon (Tables B2 and C2). However, the present invention provides compounds wherein the 6r and 5r rings may contain 0, 1, 2, 3 or 5 nitrogens. The structures in Tables B and C are shown with zero or one nitrogen merely for convenience, and to show the possible ring sizes and locations. Also, the rings in Tables B and C are shown with completely saturated rings other than the 6c ring, however, the present invention provides that any of the rings other than 6c (which is always unsaturated) may be saturated or unsaturated.

TABLE B1

|   | 5l-6c-CC-5r-5rr | 5l-6c-CC-6r-5rr | 6l-6c-CC-6r-5rr |
|---|---|---|---|
| A | | | |
| B | | | |
|   | 5ll-5l-6c-CC-5r | 5ll-5l-6c-CC-6r | 5ll-5l-6c-CC-6r |
| C | | | |
| D | | | |

TABLE B2

|   | 5l-6c-CN-5r-5rr | 5l-6c-CN-6r-5rr | 6l-6c-CN-6r-5rr |
|---|---|---|---|
| A | | | |
| B | | | |
| C | | | |
|   | 5ll-5l-6c-CN-5r | 5ll-5l-6c-CN-6r | 5ll-6l-6c-CN-6r |
| D | | | |

TABLE B2-continued
E 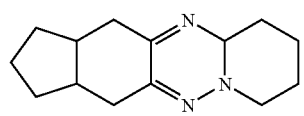
F 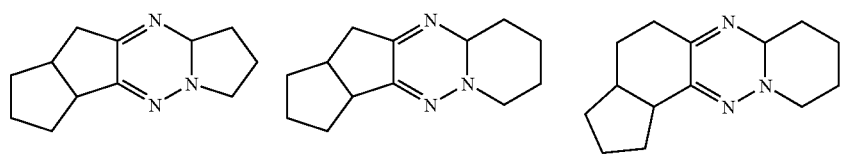
TABLE C1
| 5l-6c-CC-5r-6rr | 5l-6c-CC-6r-6rr | 6l-6c-CC-6r-6rr |
|---|---|---|
A 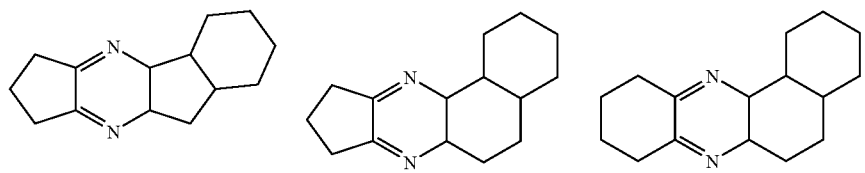
B 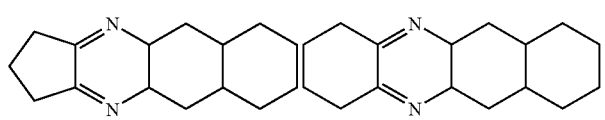
| 6ll-5l-6c-CC-5r | 6ll-5l-6c-CC-6r | 6ll-6l-6c-CC-6r |
|---|---|---|
C 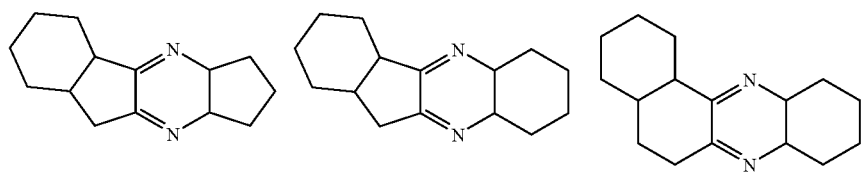
D 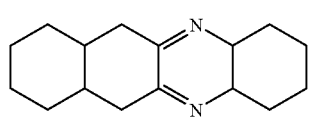
TABLE C2
| 5l-6c-CN-5r-6rr | 5l-6c-CN-6r-6rr | 6l-6c-CN-6r-6rr |
|---|---|---|
A 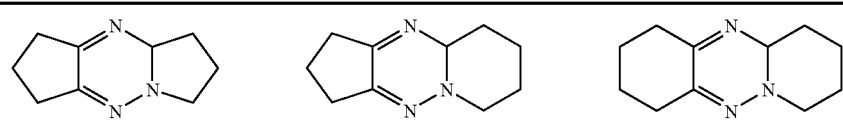
B 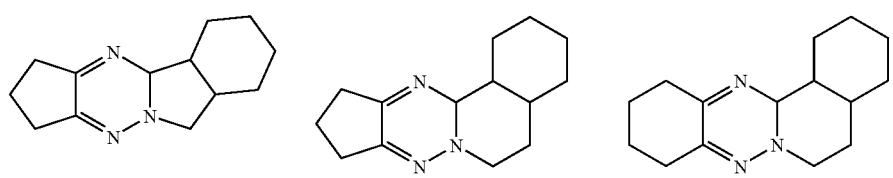

TABLE C2-continued

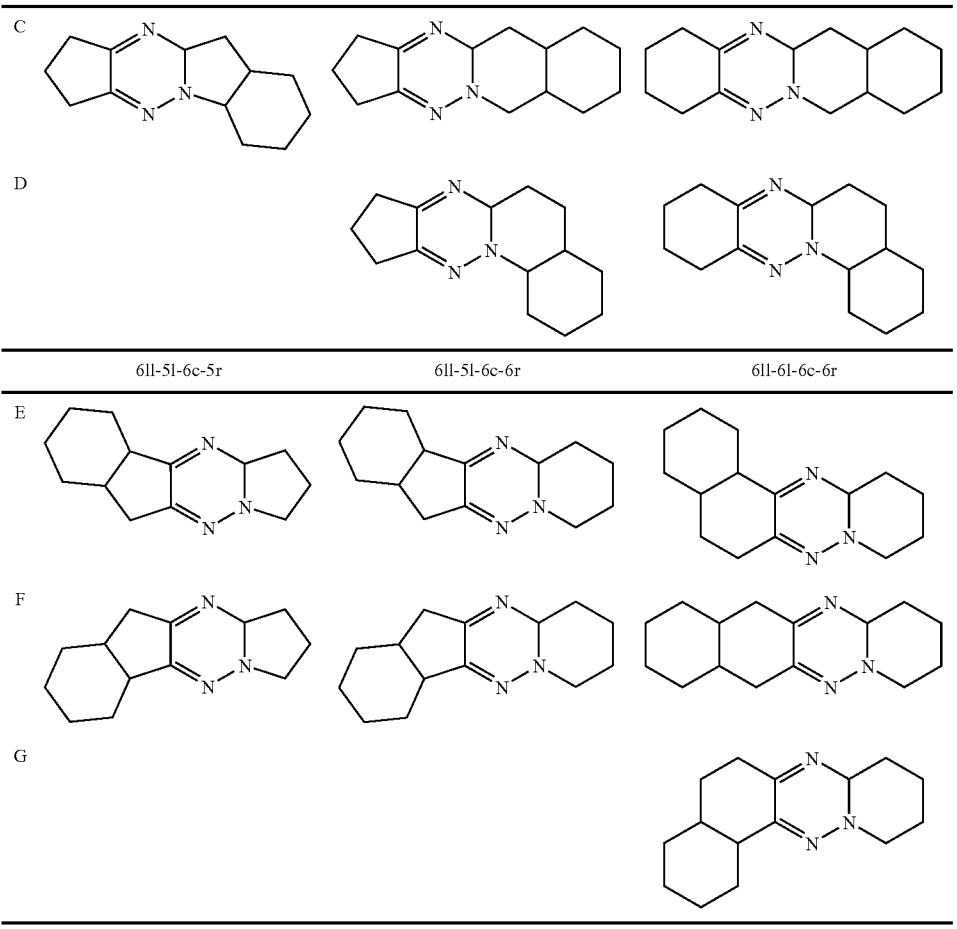

| 6ll-5l-6c-5r | 6ll-5l-6c-6r | 6ll-6l-6c-6r |

In compounds of the invention having a structure as set forth above, $R^1$ may be a C1–C20 group selected from alkyl (e.g., alkyl and cycloalkyl, such as ethyl, propyl, butyl, hexyl, cyclohexyl, and adamantyl), heteroalkyl (e.g., $CH_3CH_2$—O-carbonyl, furanyl-carbonyl, hexyl-carbonyl, and adamantyl-carbonyl), aryl (e.g., phenyl and naphthyl), and heteroaryl (e.g., pyridyl). $R^2$ may be selected from alkylarylene (e.g., methylphenyl, ethylphenyl and cyclohexylphenyl), heteroalkylarylene (e.g., bromophenyl and methoxyphenyl), alkylheteroarylene (e.g., methylpyridyl), heteroalkylheteroarylene (e.g., methoxypyridyl), arylalkylene (e.g., phenylmethylene (i.e., benzyl) and phenylethylene), heteroarylalkylene (e.g., pyridyl-$CH_2$—), arylheteroalkylene (e.g., phenylcarbonyl (i.e., benzoyl), naphthylcarbonyl, and phenyl-$CH_2CH_2$-carbonyl), heteroarylheteroalkylene (e.g., pyridyl-carbonyl), arylarylene (e.g.; biphenyl), heteroarylarylene (e.g., pyridyl-phenyl), heteroarylheteroarylene (e.g., pyridyl—pyridyl), and arylheteroarylene (e.g., phenyl-pyridyl).

In addition, $R^1$ and $R^2$ may be selected from alkyl, heteroalkyl, aryl, heteroaryl, heterocycloalkyl, cycloalkylalkylene, arylalkylene, heteroarylalkylene, heterocycloalkylalkylene; alkyl-O, heteroalkyl-O, aryl-O, heteroaryl-O, cycloalkyl-O, heterocycloalkyl-O, cycloalkylalkylene-O, arylalkylene-O, heteroarylalkylene-O, heterocycloalkylalkylene-O; alkyl-CO, heteroalkyl-CO, aryl-CO, heteroaryl-CO, cycloalkyl-CO, heterocycloalkyl-CO, cycloalkylalkylene-CO, arylalkylene-CO, heteroarylalkylene-CO, heterocycloalkyl alkylene-CO; alkyl-CONH, heteroalkyl-CONH, aryl-CONH, heteroaryl-CONH, cycloalkyl-CONH, heterocycloalkyl-CONH, cycloalkylalkylene-CONH, arylalkylene-CONH, heteroarylalkylene-CONH, heterocycloalkylalkylene-CONH; alkyl-OCO, heteroalkyl-OCO, aryl-OCO, heteroaryl-OCO, cycloalkyl-OCO, heterocycloalkyl-OCO, cycloalkylalkylene-OCO, arylalkylene-OCO, heteroarylalkylene-OCO, heterocycloalkylalkylene-OCO; alkyl-$SO_2$, heteroalkyl-$SO_2$, aryl-$SO_2$, heteroaryl-$SO_2$, cycloalkyl-$SO_2$, heterocycloalkyl-$SO_2$, cycloalkylalkylene-$SO_2$, arylalkylene-$SO_2$, heteroarylalkylene-$SO_2$, and heterocycloalkylalkylene-$SO_2$.

Specific compounds of the present invention are set forth in Table D. Biological activity for compounds of the invention are set forth in Table 1.

TABLE D

| Code | Structure |
|---|---|
| KP-23172-000 | 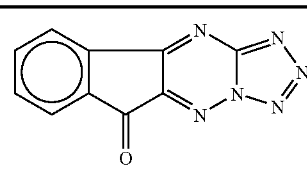 |

TABLE D-continued

| Code | Structure |
|---|---|
| KP-23172-001 | 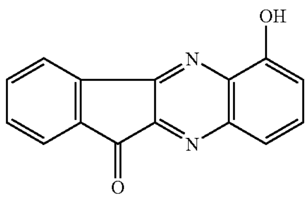 |
| KP-23172-002 | 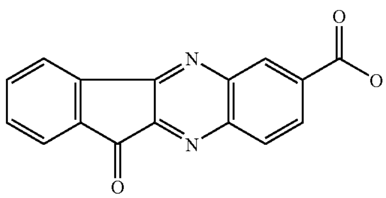 |
| KP-23172-003 | 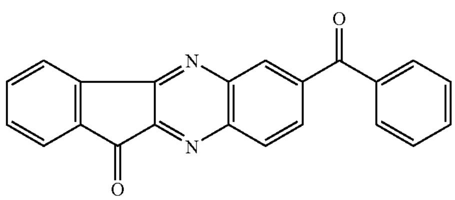 |
| KP-23172-004 | 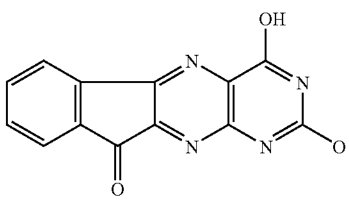 |
| KP-23172-005 | 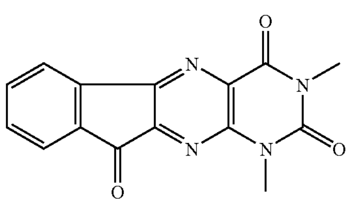 |
| KP-23172-006 | 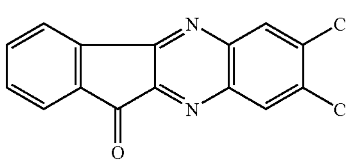 |
| KP-23172-007 | 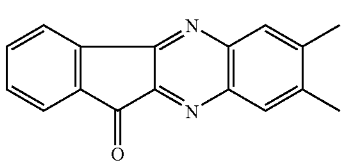 |
| KP-23172-008 | 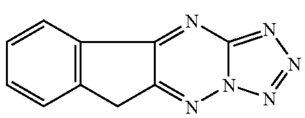 |
| KP-23172-009 | |
| KP-23172-010 | |
| KP-23172-011 | |
| KP-23172-012 | |
| KP-23172-013 | |
| KP-23172-014 | |
| KP-23172-015 | |
| KP-23172-016 | |

TABLE D-continued
| Code | Structure |
|---|---|
| KP-23172-017 | 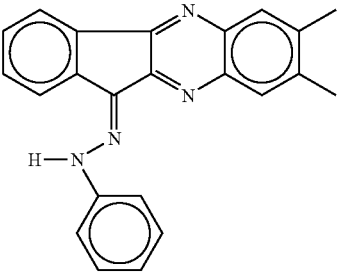 |
| KP-23172-018 | 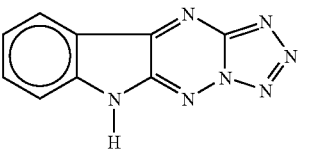 |
| KP-23172-019 | 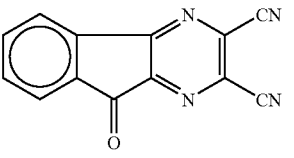 |
| KP-23172-020 | 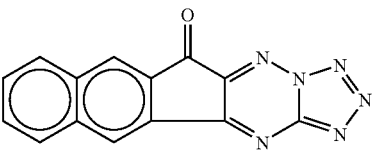 |
| KP-23172-021 | 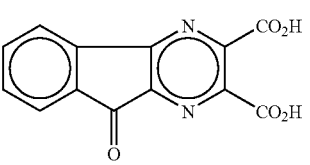 |
| KP-23172-022 | 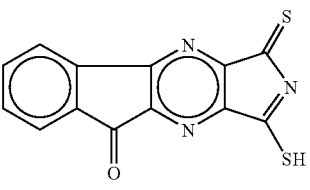 |
| KP-23172-023 | 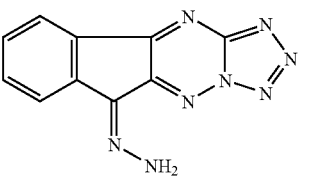 |
| KP-23172-024 | 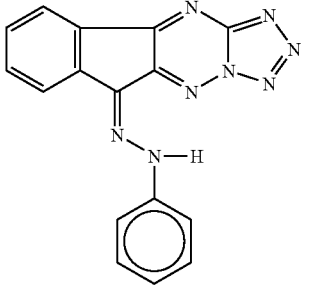 |
| KP-23172-025 | 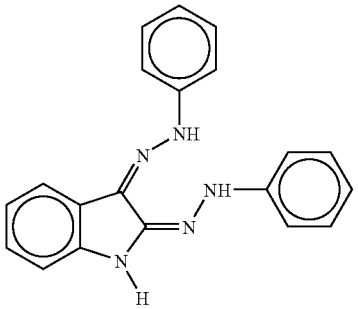 |
| KP-23172-026 | 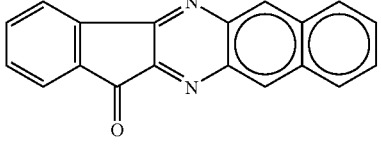 |
| KP-23172-027 | 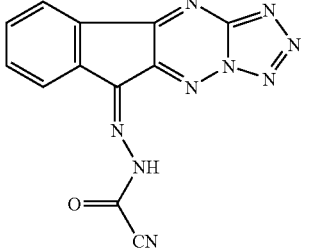 |
| KP-23172-028 | 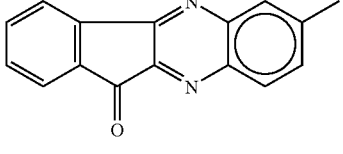 |
| KP-23172-029 | 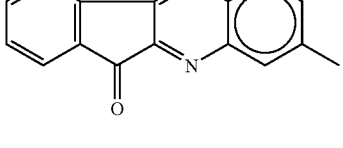 |
| KP-23172-030 | 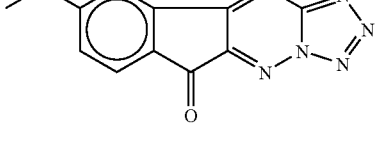 |

TABLE D-continued

| Code | Structure |
|---|---|
| KP-23172-031 | 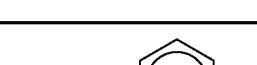 |

Compounds of the present invention may be prepared by condensation of an ortho dione (such as isatin and 1,2-indanedione) or trione (such as ninhydrin) compound and an ortho diamino compound (such as 1,5-diaminotetrazole and 4,5-diamino-1,2,3-triazole). The general reaction scheme is illustrated in Scheme 1.

Scheme 1

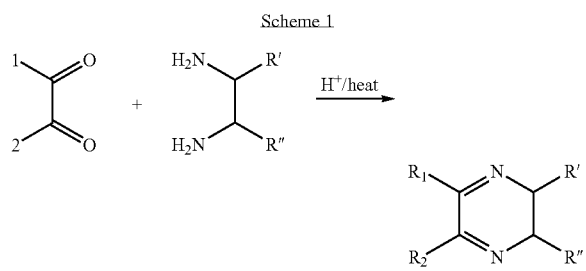

Ninhydrin itself is commercially available from, e.g., Aldrich (Milwaukee, Wis.; www.sigma-aldrich.com). Many substituted ninhydrins (triones) are also known and may be used to prepare compounds of the present invention. See, e.g., "Synthesis of fingerprint reagents. Aromatic nucleophilic substitution as a route to 5-substituted ninhydrins" by Della, Ernest W.; Janowski, Wit K.; Pigou, Paul E.; and Taylor, Bruce M., Synthesis (1999), (12), 2119–2123; "A convenient one-pot synthesis of indane-1,2,3-triones by oxidation of indan-1-ones with N-bromosuccinimide-dimethyl sulfoxide reagent" by Tatsugi, Jiro; and Izawa, Yasuji, Synth. Commun. (1998), 28(5), 859–864; "Investigation of anhydrous benzo(f)ninhydrin, indanetrione and 5-methoxy indanetrione by electronic absorption and emission spectroscopy and computational chemistry methods" by Roy, J.; Bhattacharya, S.; Ghosh, Sanjib; Majumder, D.; and Bhattacharyya, S. P., Chem. Phys. (1997), 222(2,3), 161–173; "The hydration of indane-1,2,3-triones and related triones" by Bowden, Keith; and Rumpal, Sanjay, J. Chem. Res., Synop. (1997), (2), 35; "Synthesis of 2-acyl-1-benzyl-, 1-phenylethyl- and spirobenzyltetrahydroisoquinolines" by Venkov, A. P.; and Lukanov, L. K., Synth. Commun. (1996), 26(4), 755–62; and "Synthesis and some reactions of polyfluorinated 1,3-indandiones. II" by Qsadchii, S. A.; and Barkhash, V. A.; Zh. Org. Khim. (1970), 6(9), 1815–20.

Likewise, many diamino compounds of Scheme 1 are known and may be used in the synthesis of compounds of the present invention. For representative examples of 5-membered rings having 1,2-diamine substitution, and methods of preparing same, see, e.g., Chem. Heterocycl. Compd. (N.Y.) (2000), Volume Date 1999, 35(7), 882–883; PCT International Publication No. WO 2000002051; PCT International Publication No. WO 2000002050; U.S. Pat. No. 6,004,410; Tetrahedron: Asymmetry (1999), 10(20), 3887–3891; PCT Int. Publication No. WO 9951546; Synlett (1999), (9), 1413–1414; PCT Int. Publication No. WO 9940882; Synth. Met. (1999), 101(1–3), 532–533; J. Heterocycl. Chem. (1999), 36(3), 635–638; J. Porphyrins Phthalocyanines (1999), 3(5), 371–379; Russ. J. Org. Chem. (1998), 34(7), 1026–1031; Nucl. Med. Biol. (1999), 26(2), 217–224; Proc. Int. Pyrotech. Semin. (1997), 23rd, 782–791; Proc. Natl. Acad. Sci. U.S.A. (1998), 95(23), 13525–13530; Comb. Chem. High Throughput Screening (1998), 1(3), 135–142; Bull. Korean Chem. Soc. (1998), 19(10), 1119–1121; J. Heterocyc. Chem. (1998), 35(4), 923–926; Bull. Chem. Soc. Jpn. (1998), 71(10), 2387–2391; PCT Int. Publication No. WO 9840396; Chem. Commun. (Cambridge) (1998), (19), 2081–2082; Chin. Sci. Bull. (1998), 43(16), 1395–1399; Chem. Heterocycl. Compd. (N.Y.) (1998), Volume Date 1997, 33(12), 1473–1474; Int. Annu. Conf. ICT (1998), 29th(Energetic Materials), 170.1–170.11; Russ. J. Org. Chem. (1997), 33(11), 1656–1665; Biospectroscopy (1998), 4(3), 197–208; J. Heterocycl. Chem. (1998), 35(2), 297–300; Chem. Mater. (1998), 10(5), 1236–1243; U.S. Pat. No. 5,741,998; Bull. Korean Chem. Soc. (1998), 19(2), 252–254; J. Raman Spectrosc. (1998), 29(3), 229–236; Bioorg. Med. Chem. Lett. (1998), 8(5), 525–528; J. Heterocycl. Chem. (1998), 35(1), 151–155; PCT Int. Publication No. WO 9808839; Chem. Mater. (1998), 10(1), 3–5; Chem. Heterocycl. Compd. (N.Y.) (1997), 33(3), 276–281; Spectrosc. Biol. Mol.: Mod. Trends, [Eur. Conf.], 7th (1997), 355–356, Editor(s): Carmona, Pedro; Navarro, Raquel; Hernanz, Antonio. Publisher: Kluwer, Dordrecht, Neth.; Struct. Chem. (1997), 8(5), 373–377; Tetrahedron Lett. (1997), 38(38), 6751–6754; Placenta (1997), 18(7), 527–533; Tetrahedron (1997), 53(30), 10331–10344; J. Chem. Res., Synop. (1997), (7), 250–251; Bioorg. Med. Chem. Lett. (1997), 7(13), 1733–1738; J. Heterocycl. Chem. (1997), 34(3), 1057–1060; Tetrahedron: Asymmetry (1997), 8(11), 1861–1867; J. Heterocycl. Chem. (1997), 34(2), 629–632; Sulfur Rep. (1996), 19(1), 215–284; i(1997), 30(3), 673–675; U.S. Pat. No. 5,583,141; J. Chem. Soc., Perkin Trans. 1 (1996), (22), 2675–2684; J. Am. Chem. Soc. (1996), 118(50), 12521–12527; Mendeleev Commun. (1996), (5), 193–195; PCT Int. Publication No. WO 9628449; Proc. Int. Pyrotech. Semin. (1996), 22nd, 377–388; J. Org. Chem. (1996), 61(18), 6086–6087; J. Inclusion Phenom. Mol. Recognit. Chem. (1995), 23(3), 181–193; U.S. Pat. No. 5,514,505; Proc. Beijing Int. Symp. Pyrotech. Explos., 3rd (1995), 249–254, Editor(s): Yuxiang, Ou. Publisher: China Ordnance Society, Beijing, Peop. Rep. China; Mendeleev Commun. (1996), (2), 66–67; U.S. Pat. No. 5,500,439; Acta Crystallogr., Sect. C: Cryst. Struct. Commun. (1995), C51 (12), 2594–5; PCT Int. Publication No. WO 9520590; PCT Int. Publication No. WO 9519567; Report (1995), Order No. AD-A292429, 10 pp. Avail.: NTIS, From: Gov. Rep. Announce. Index (U.S.) 1995, 95(21), Abstr. No. 21-03,268; PCT Int. Publication No. WO 9521172; J. Mater. Chem. (1995), 5(9), 1285–90; PCT Int. Publication No. WO 9515978; J. Org. Chem. (1995), 60(20), 6309–17; PCT Int. Publication No. WO 9403271; J. Heterocycl. Chem. (1995), 32(4), 1405–7; J. Med. Chem. (1995), 38(18), 3524–35; Heterocycles (1995), 41(3), 497–506; Mendeleev Commun. (1995), (2), 56–8; J. Heterocycl. Chem. (1995), 32(1), 169–76; Tetrahedron (1995), 51(2), 567–78; Tetrahedron Lett. (1994), 35(46), 8557–60; Aust. J. Chem. (1994), 47(11), 2033–45; Biochem. Biophys. Res. Commun. (1994), 204(2), 962–8; J. Mol. Biol. (1994), 242(4), 559–65; Pharmazie (1994), 49(10), 727–9; Mendeleev Commun. (1994), (4), 138–40; *Report* (1992), TR-39; Order No. AD-A256653, 9 pp. Avail.: NTIS, From: Gov. Rep. Announce. Index (U.S.) 1993, 93(3), Abstr. No. 306,166; *Heterocycles* (1994), 37(2), 693–6; *Heteroat. Chem.* (1993), 4(5), 521–4; *J. Heterocycl. Chem.* (1993), 30(5), 1379–83; *Heterocycles* (1993), 36(10), 2397–405; *Bioorg. Med. Chem. Lett.* (1994), 4(1), 35–40; *J. Org. Chem.* (1993), 58(17), 4696–702; *Synth. Met.* (1993), 55(2–3), 960–5; Eur. Pat. Appl. No. EP 520423; *Chim. Acta Turc.* (1992), Volume Date 1991, 19(1), 27–39; *J. Labelled Compd. Radiopharm.* (1992), 31(12), 1065–70; *J. Chem. Soc., Perkin Trans.* 2 (1992), (9), 1643–6; *J. Am. Chem. Soc.* (1992), 114(24), 9538–44; *Heterocycles* (1992), 34(6), 1191–200; *J. Polym. Sci., Part A: Polym. Chem.* (1992), 30(9), 2059–62; U.S. Pat. No. 5,463,073; U.S. Pat. No. 5,182,279; and *Arch. Pharm.* (Weinheim, Ger.) (1992) 325(4), 225–34.

For representative examples of 5-membered rings having 1,2-diamine substitution, where one of the diamine groups is substituted on a ring carbon atom and the other diamine group is substituted on an adjacent ring nitrogen atom, and methods for preparing same, see, e.g., *Indian J. Chem., Sect. B: Org. Chem. Incl. Med. Chem.* (1999), 38B(8), 998–1001; *Farmaco* (1999), 54(11–12), 800–809; *J. Heterocycl. Chem.* (1999), 36(5), 1317–1321; *Chem. Heterocycl. Compd. (N.Y.)* (1999), 35(3), 374–375; PCT Int. Publication No. WO 9948896; *Pharmazie* (1999), 54(8), 580–587; PCT Int. Publication No. WO 9938508; *Chem. Heterocycl. Compd. (N.Y.)* (1999), Volume Date 1998, 34(10), 1189–1194; *J. Chem. Soc., Perkin Trans.* 1 (1999), (10), 1339–1346; *Chem. Heterocycl. Compd. (N.Y.)* (1998), 34(4), 488–491; *Chem. Heterocycl. Compd. (N.Y.)* (1998), 34(2), 232–236; *Nucleosides Nucleotides* (1998), 17(8), 1385–1407; *Z. Naturforsch., B: Chem. Sci.* (1997), 52(7), 873–882; PCT Int. Publication No. WO 9629361; PCT Int. Publication No. WO 9622979; *Indian J. Heterocycl. Chem.* (1996), 5(3), 215–218; *Bioorg. Med. Chem. Lett.* (1995), 5(15), 1573–6; *J. Heterocycl. Chem.* (1995), 32(2), 457–62; U.S. Pat. No. 5,358,960; *Heterocycles* (1994), 37(2), 997–1018; *Bull. Chem. Soc. Jpn.* (1994), 67(1), 149–55; U.S. Pat. No. 5,326,779; *J. Chem. Res., Synop.* (1993), (7), 260–1; *Chromatographia* (1993), 37(1–2), 98–104; *Mendeleev Commun.* (1993), (3), 111; U.S. Pat. No. 5,140,048; *J. Chem. Soc., Perkin Trans.* 1 (1992), (7), 913–17; *Biosci., Biotechnol., Biochem.* (1992), 56(2), 199–206; *Indian J. Chem., Sect. B* (1991), 30B(12), 1119–23; *Bull. Chem. Soc. Jpn.* (1992), 65(2), 546–52; *J. Heterocycl. Chem.* (1990), 27(7), 1941–5; *J. Org. Chem.* (1991), 56(1), 74–8; *J. Heterocycl. Chem.* (1990), 27(4), 1109–10; *Heterocycles* (1990), 31(2), 267–76; *J. Heterocycl. Chem.* (1989), 26(4), 1077–81; U.S. Pat. No. 5,126,442; *J. Heterocycl. Chem.* (1989), 26(4), 1109–12; *J. Chem. Res., Synop.* (1989), (6), 156–7; *J. Med. Chem.* (1990), 33(1), 298–307; *Tetrahedron* (1988), 44(23), 7185–92; *J. Heterocycl. Chem.* (1988), 25(2), 565–70; *J. Heterocycl. Chem.* (1988), 25(3), 791–4; *J. Org. Chem.* (1988), 53(22), 5371–4; *Chem. Pharm. Bull.* (1987), 35(10), 4031–8; *Tetrahedron* (1986), 42(10), 2625–34; *Synthesis* (1986), (1), 71–4; U.S. Pat. No. 4,497,793; *J. Org. Chem.* (1981), 46(20), 4065–8; *J. Heterocycl. Chem.* (1979), 16(7), 1393–403; *Heterocycles* (1979), 12(8), 100–14; U.S. Pat. No. 4,159,375; *J. Org. Chem.* (1978), 43(13), 2693–6; *Z. Naturforsch., B: Anorg. Chem., Org. Chem.* (1977), 32B(5), 569–72; *J. Org. Chem.* (1977), 42(6), 1018–22; *J. Heterocycl. Chem.* (1976), 13(6), 1219–24; *J. Org. Chem.* (1977), 42(3), 542–5; *Synth. Commun.* (1976), 6(6), 457–60; *Tetrahedron Lett.* (1976), (12), 903–4; *J. Heterocycl. Chem.* (1974), 11(3), 327–9; *J. Org. Chem.* (1973), 38(18), 3084–6; *J. Chem. Soc., Perkin Trans.* 2 (1973), (1), 1–3; *J. Heterocycl. Chem.* (1972), 9(5), 1171–3; *Jap. Pestic. Inform.* (1972), No. 12, 15–17; U.S. Pat. No. 3,697,244; *J. Nat. Cancer Inst.* (1972), 48(3), 783–90; *J. Chem. Soc., Perkin Trans.* 1 (1972), (9–10), 1221–5; *J. Heterocycl. Chem.* (1972), 9(1), 153–4; *Chem. Ind. (London)* (1970), 50, 1594–5; *Can. J. Chem.* (1969), 47(19), 3677–81; *J. Org. Chem.* (1968); 33(1), 143–50; *J. Heterocycl. Chem.* (1967), 4(2), 272–83; and *Chem. Ind. (London)* (1966), (52), 2168–9.

Pharmaceutical Formulations

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the inhibitory compounds is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of the provided inhibitory compounds and other cytotoxic agents has the advantages that the required dosages for the individual drugs is lower, and the effect of the different drugs complementary. Depending on the patient and condition being treated and on the administration route, the subject inhibitory compounds may be administered in dosages of 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with other pharmaceutically active agents, particularly other anti-metastatic, anti-tumor or anti-angiogenic agents. Angiostatic compounds of interest include angiostatin, endostatin, carboxy terminal peptides: of collagen alpha (XV), etc. Cytotoxic and cytostatic agents of interest include adriamycin, alkeran, Ara-C, BICNU, busulfan, CNNU, cisplatinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

Methods of Use

The subject compounds are administered to a subject having a hyperproliferative disorders, e.g. to inhibit tumor growth, to decrease inflammation associated with a lymphoproliferative disorder, to inhibit graft rejection, or neurological damage due to tissue repair, etc. Of particular interest is the inhibition of anti-apoptotic signals in proliferating cell populations.

The present compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g. to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one hour and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g. at least about 50%, decrease in the cell burden, and may be continued until there are essentially none of the undesirable cells detected in the body.

The compounds also find use in the specific inhibition of signaling pathway mediated by protein kinases. Protein kinases are involved in signaling pathways for such important cellular activities as responses to extracellular signals and cell cycle checkpoints. Inhibition of specific protein kinases provides a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in signaling mediated by protein kinases. Such conditions include those associated with defects in cell cycle regulation or in response to extracellular signals, e.g. hyperglycemia and diabetes Type I and Type II, immunological disorders, e.g. autoimmune and immunodeficiency diseases; hyperproliferative disorders, which may include psoriasis, arthritis, inflammation, endometriosis, scarring, cancer, etc.

The compounds of the present invention are active in inhibiting purified kinase proteins, i.e. there is a decrease in the phosphorylation of a specific substrate in the presence of the compound. A protein kinase of particular interest in protein kinase B (PBK; ATK). The protein kinase B sequence is described by Coffer and Woodgett (1991) Eur. J. Biochem. 201(2):475–481, and may be found in Genbank, accession number X61037. PKB is a widely expressed cytoplasmic serine-threonine kinase, and its aberrant expression has been implicated in tumorigenesis. PKB contains at its NH2-terminus a domain termed the pleckstrin homology (PH) domain, which may regulate the activation of PKB by binding D3-phosphorylated phosphoinositides that are the products of P13-K. Phosphorylation of PKB also influences its activation, and the PH domain may influence the activation of PKB by promoting its dimerization. Phosphorylation of GSK-3 by PKB is believed to regulate glycogen synthesis. Activation of PKB is blocked by wortmannin and by LY294002.

PKB is also involved in pathways leading to nitric oxide production. PKB directly phosphorylates eNOS, and activates the enzyme leading to nitric oxide (NO) production. Inhibition of PKB attenuates NO production stimulated by VEGF. Phosphorylation of eNOS by PKB is a calcium-independent regulatory mechanism for activation of eNOS.

The compounds of the present invention bind to protein kinases at a high affinity, and find use as affinity reagents for the isolation and/or purification of such kinases. Affinity chromatography is used as a method of separating and purifying protein kinases and phosphatases using the biochemical affinity of the enzyme for inhibitors that act on it. The compounds are coupled to a matrix or gel. Preferably a microsphere or matrix is used as the support. Such supports are known in the art and commercially available. The inhibitor coupled support is used to separate an enzyme that binds to the inhibitor from a complex mixture, e.g. a cell lysate, that may optionally be partially purified. The sample mixture is contacted with the inhibitor coupled support under conditions that minimize non-specific binding. Methods known in the art include columns, gels, capillaries, etc. The unbound compounds are washed free of the resin, and the bound proteins are then eluted in a suitable buffer.

The compounds of the invention may also be useful as reagents for studying signal transduction or any of the clinical disorders listed throughout this application.

Hyper-Proliferative Disorders of Interest

There are many disorders associated with a dysregulation of cellular proliferation. The conditions of interest include, but are not limited to, the following conditions.

The subject methods are applied to the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g. uterine, testicular and ovarian carcinomas, endometriosis, squamous and glandular epithelial carcinomas of the cervix, etc. are reduced in cell number by administration of the subject compounds Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Tumors of neural tissue are of particular interest, e.g. gliomas, neuromas, etc.

Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Reactants and reagents used in the following examples may be obtained from commercial supply houses known to those of skill in the art, including Aldrich (Milwaukee, Wis., USA; www.aldrich.sial.com); EM Industries, Inc. (Hawthorne, N.Y., USA; www.emscience.com); Lancaster Synthesis, Inc. (Windham, N.H., USA; www.lancaster.co.uk); Maybridge Chemical Company Ltd. (Trevilleft, U.K.; www.maybridge.co.uk); Spectrum Quality Product, Inc. (New Brunswick, N.J., USA; www.spectrumchemical.com); and TCI America (Portland, Oreg., USA; www.tciamerica.com). Unless otherwise indicated, the reactants and reagents were analytical grade or better and were used without further purification. Compounds (including starting materials) which are not commercially available can be prepared by employing known methods from the chemical literature, including methods set forth in the references identified above.

EXAMPLES

Example 1

Synthesis of KP-23172

In a 250 mL round-bottom flask, equipped with a condenser and magnetic stir bar, was placed ninhydrin (5.9 g, 33 mmol), concentrated hydrochloric acid (0.3 mL) and water (70 mL). This solution was warmed up to 60° C. with stirring. 1,5-diaminotetrazole (3.0 g, 30 mmol) was added in small portions over 5 min. The solution was then heated to reflux for 30 min and cooled. The crude product was collected on a funnel and washed with water (5.56 g, 83%). The crude product (600 mg) was purified by chromatography on silica gel eluting with chloroform/ethanol (98:2) to give a light yellow powder (550 mg). TLC analysis (ethyl acetate/hexanes 1:1) and NMR spectra indicated that the product consisted of KP-23172 and an isomer thereof (KP-17483) in a ratio of about 1:1. $^1$H NMR (DMSO-$d_6$, ppm, mixture of two isomers): 8.35 (m, 1H), 8.2–7.9 (m, 3H). $^{13}$C NMR (DMSO-$d_6$, ppm, mixture of two isomers): 123.99, 124.64, 125.21, 125.34, 135.29, 136.10, 136.32, 137.89, 138.28, 138.33, 138.71, 139.49, 148.91, 149.56, 149.85, 153.83, 157.92, 162.50, 183.13, 184.16. Mass spectrum (EI, m/e): 224 (M$^+$), 196, 168, 140, 88 (100%).

Example 2

Synthesis of KP-23172-001

Ninhydrin (0.160 g, mmol) and 2,3-diaminophenol (0.100 g, mmol) were dissolved in mL of anhydrous ethanol. The resulting solution was heated to 80° C. in an oil bath and 0.2 mL of glacial acetic acid was then added. The mixture was then refluxed for two hours. Upon cooling, filtration, and washing the product with water, the desired product was obtained as golden yellow granules in 72% yield. $^1$H NMR (ppm) 10.6, 8.2, 8.0, 7.7, 7.3, 7.2. FTIR spectrum (KBr pellet, cm$^{-1}$): 3445, 1718, 1580, 1518, 1479, 1196.

Examples 3A–3N

Additional Compounds Prepared by Method of Example 2

Example 3A—KP-23172-002: This compound, obtained as light yellow crystals, was synthesized using 3,4-diaminobenzoic acid (0.130 g, mmol) and ninhydrin (0.100 g, mmol) in 93% yield. $^1$H NMR (ppm): 10.6, 8.6, 8.4, 8.3. FTIR spectrum (KBr pellet, cm$^{-1}$): 2978, 1731, 1707, 1602, 1574, 1305, 1273.

Example 3B—KP-23172-003: This compound, obtained as orange granular crystals, was synthesized using 3,4-diaminobenzophenone (0.100 g, mmol) and ninhydrin (0.090 g, mmol) in 51% yield. IR spectrum (KBr pellet, cm$^{-1}$): 3432, 3060, 1727, 1660, 1650, 1578, 1338, 1308, 1193, 721.

Example 3C—KP-23172-004: This compound, obtained as orange granular crystals was synthesized using 5,6-diamino-2,4-dihydroxypyrimidine sulfate (0.115 g, mmol) and ninhydrin (0.100 g, mmol) with 57% yield. IR spectrum (KBr pellet, cm$^{-1}$): 3472, 3199, 2730, 1722, 1683, 1642, 1567, 1456, 1366, 1204.

Example 3D—KP-23172-005: This compound, obtained as copper brown granules, was synthesized using 5,6-diamino-1,3-dimethyluracil hydrate (0.120 g mmol) and ninhydrin (0.150 g mmol) in 68% yield. IR spectrum (KBr pellet, cm$^{-1}$): 3429, 3069, 2946, 1729, 1672, 1575, 1561, 1505, 1354, 1254, 1235.

Example 3E—KP-23172-006: This compound, obtained as a dark green powder, was synthesized using 4,5-dichloro-1,2-phenyldiamine 0.100 g, mmol) and ninhydrin (0.100 g, mmol) in 60% yield. IR spectrum (KBr pellet, cm$^{-1}$): 3439, 3052, 1735, 1613, 1564, 1479, 1396, 1331, 732.

Example 3F—KP-23172-007: This compound, obtained as yellow prism crystals, was synthesized using 4,5-dimethyl-1,2-phenyldiamine (0.110 g, mmol) and ninhydrin (0.155 g, mmol) with 67% yield. IR spectrum (KBr pellet, cm$^{-1}$): 3439, 2947, 2918, 1720, 1604, 1557, 1495. Mass spectrum (EI, m/e): 260, 245, 232, 217, 201, 130, 103, 78, 77, 51.

Example 3G—KP-23172-009: This compound was synthesized using 4,5-diamino-6-hydroxypyrimidine (0.140 g, mmol) and ninhydrin (0.220 g, mmol) and was obtained as light yellow granules in 99% yield.

Example 3H—KP-23172-010: This compound was synthesized using 4,5-diamino-6-hydroxypyrimidine (0.100 g, mmol) and 1,2-naphthoquinone (0.130 g, mmol) and was obtained as a dark brown powder after being recrystallized from hot ethanol.

Example 3I—KP-23172-011: This compound was synthesized using 1,5-diaminotetrazole (0.100 g, mmol) and 1,2-naphthoquinone (0.107 g, mmol). The product was obtained as a dark brown powder after being recrystallized from hot ethanol.

Example 3J—KP-23172-012: This compound was synthesized using 2,3-diaminophenol 0.110 g mmol) and 1,2-naphthoquinone (0.135 g, mmol). The product was obtained as a dark brown powder after being recrystallized from hot ethanol.

Example 3K—KP-23172-013: This compound was synthesized using 4,5-dimethyl-1,2-phenyldiamine (0.110 g, mmol) and 1,2-naphthoquinone (0.130 g, mmol). The product was obtained as a dark brown powder after being recrystallized from hot ethanol.

Example 3L—KP-23172-014: This compound was synthesized using 1,5-diaminotetrazole (0.110 g, mmol) and 2,3-butanedione (0.170 g, mmol). The product was obtained as white needle crystals after being recrystallized from boiling water (yield 6%). m.p.:135° C. IR spectrum (KBr pellet, cm$^{-1}$): 2917, 1588, 1529, 1500, 1394, 1300, 1285, 1091. Mass spectrum (EI, m/e): 150, 93, 79, 77, 69, 67, 54.

Example 3M—KP-23172-026: This compound was synthesized using 2,3-diaminonaphthlene (0.160 g, mmol) and ninhydrin 0.130 g mmol) and was isolated as orange needle-like crystals after being recrystallized from hot water. Yield 90%; m.p. 290° C.

Example 3N—KP-23172-028: This compound was synthesized using 2,3-diaminotoluene (0.2 mL, mmol) and ninhydrin (0.155 g, mmol). The product was isolated as yellow needle crystals after being recrystallized from hot methanol.

Example 4

Synthesis of KP-23172-008

1,2-Indandione (0.115 g, mmol) and 1,5-diaminotetrazole 0.100 g, mmol) were dissolved separately in a mixture of glacial acetic acid and water (1:1) in 100 mL round bottom flasks. The solutions were warmed up to 60° C. and stirred for 30 minutes. They were then mixed and kept under reflux for two hours. The crystals obtained upon cooling to 0° C. were isolated by filtration and washed with ethanol. The product was obtained as light brown crystals after being recrystallized from hot ethanol. Yield 18%; IR spectrum (KBr pellet, cm$^{-1}$) 3320, 3137, 1726, 1660, 1604, 1582, 1457 1338, 1301, 1243, 1160, 1048.

Example 5

Synthesis of KP-23172-018

1,5-Diaminotetrazole (0.100 g, mmol) and isatin (0.150 g, mmol) were dissolved separately in a mixture of glacial acetic acid and water (1:1). The solutions were were heated to 60° C. and stirred for 30 minutes. They were then mixed and kept under reflux for two hours. The crystals obtained upon cooling to 0° C. were isolated by filtration and washed with ethanol. The product was purified by preparative thin layer chromatography using 5% methanol and 95% methylene chloride as developing solvent and obtained as orange granular crystals.

Example 6

Synthesis of KP-23173-015

In a round-bottom flask, equipped with a condenser and magnetic stir bar, was placed ninhydrin (0.500 g, 2.81 mmol), concentrated hydrochloric acid (28 μL) and water (3.5 mL). This solution was warmed up to 60° C. with stirring. Cis and trans 1,2-diaminocyclohexane (0.400 g, 30 mmol) was added in one portion. The solution was then heated to reflux for 30 min and cooled. The product was collected on a funnel and washed with water (0.620 g dark purple solid). The product was heated to reflux in EtOH/acetic acid (3:1) for 5 h and cooled. The crude product was collected by filtration and washed with water, and purified by chromatography on silica gel eluting with ethyl acetate/hexanes (0–40%) to give a red powder (197 mg). $^1$H NMR (DMSO-d$_6$, ppm): 7.87–7.7 (m, 3H), 7.6 (m, 1H), 3.0 (m, 4H), 1.95 (broad singlet-like, 4H).

Example 7

Synthesis of KP-23172-016

In a round-bottom flask, equipped with a condenser and magnetic stir bar, was placed ninhydrin (0.500 g, 2.81 mmol), acetic acid (10 mL) and water (4 mL). This solution was warmed up to 60° C. with stirring. 1,2-Ethylenediamine (0.169 g, 2.81 mmol) was added in one portion. The solution was then heated to reflux overnight and then cooled. The solvent was removed in vacuo and the residue was purified by chromatography on silica gel eluting with ethyl acetate/hexanes (1:1) to give a yellow powder (0.100 g). $^1$H NMR (DMSO-d$_6$, ppm): 8.62 (s, 2H), 7.9 (m, 1H), 7.82–7.7 (m, 2H), 7.61 (m, 1H).

Example 8

Synthesis of KP-23172-019

In a round-bottom flask, equipped with a condenser and magnetic stir bar, was placed ninhydrin (0.500 g, 2.81 mmol), concentrated hydrochloric acid (0.025 mL) and water (6 mL). This solution was warmed up to 60° C. with stirring. 2,3-Diamino-1,4-ethanedinitrile (0.275 g, 2.55 mmol) was added in dropwise. The solution was then heated to reflux for 2 hours and then cooled. The solvent was removed in vacuo and a yellow powder was obtained (0.546 g, 92%). $^1$H NMR (CDCl3, ppm): 8.1–7.7 (m, 4H).

Example 9

Synthesis of KP-23172-021

In a round-bottom flask, equipped with a condenser and magnetic stir bar, was placed the dinitrile KP-27472 (0.100 mg, 0.43 mmol) and 6 N HCl (10 mL). This mixture was then heated to reflux overnight. Concentrated hydrochloric acid (3 mL) was added to the reaction mixture and the reaction mixture was continued to reflux for 1 h. The solvent was removed in vacuo and the residue was washed with water to give a pale solid (0.080 g). $^1$H NMR (CDCl$_3$, ppm): 8.2 (d, 1H), 7.8–7.5 (m, 3H), 4.2 (s, 2H).

Example 10

Synthesis of KP-23172-022

In a round-bottom flask, equipped with a condenser and magnetic stir bar, was placed the dinitrile KP-27472 (0.031 g) and methanol (10 mL). To this suspension was passed ammonium sulfide at room temperature for 4 min. Soon a greenish brown solution was obtained and then was heated to reflux for 2 h. The reaction mixture was diluted with water. A greenish powder was collected on a funnel, washed with water, and dried (0.029 g). $^1$H NMR (CDCl$_3$, ppm): 9.1 (s, 1H), 8.0–7.6 (m, 4H).

Example 11

Synthesis of KP-23172-031

In a round-bottom flask, equipped with a condenser and magnetic stir bar, was placed ninhydrin (0.050 g, 0.28 mmol), concentrated hydrochloric acid (one drop) and water (2 mL). This solution was warmed up to 60° C. with stirring. 9,10-Diaminophenanthrene (0.058 g, 0.28 mmol) was added in one portion. The solution was then heated to reflux for 4 h and then cooled. The product was collected on a funnel, washed with water and dried (0.090 g, 97%). $^1$H NMR (CDCl$_3$, ppm): 9.1 (d, 1H), 8.95 (d, 1H), 8.35 (m, 2H), 7.9 (m, 1H), 7.6–7.2 (m, 7H).

Example 12

Synthesis of KP23172-020

In a round-bottom flask, equipped with a condenser and magnetic stir bar, was placed benzo[f]ninhydrin (25 mg, 0.11 mmol), concentrated hydrochloric acid (0.036 mL) and water (1 mL). This suspension was warmed up to 60° C. with stirring. 1,5-Diaminotetrazole (12 mg, 0.12 mmol) was added in one portion. The mixture was then heated to reflux for 9 h and then cooled. The crude product was collected on a funnel and washed with water (9 mg, orange powder). TLC analysis (ethyl acetate/hexanes 1:1) indicates that the product consist of two isomers with a ratio of about 1:1 (2 and 3).

Example 13

Synthesis of KP-23172-030

In a round-bottom flask, equipped with a condenser and magnetic stir bar, was placed benzo[f]ninhydrin (30 mg, 0.14 mmol), concentrated hydrochloric acid (one drop) and water (1 mL). This suspension was warmed up to 60° C. with stirring. 1,5-Diaminotetrazole (22 mg, 0.22 mmol) was added in one portion. The solution was then heated to reflux for 6 h and then cooled. The crude product was collected on a funnel and washed with water (18 mg, red powder). TLC analysis (ethyl acetate/hexanes 1:1) and $^1$H NMR indicate that the product consist of two isomers with a ratio of about 1:1. $^1$H NMR (CDCl$_3$, ppm): mixture of two isomers 8.3–7.3 (m, 3H), 4.15, 4.05 (two singlets, 3H).

Example 14

PKB Inhibition In Vitro

KP-17483 was found to inhibit PKB in an in vitro enzyme assay testing a range of compounds for such activity. This compound formed the basis for a course of study in analogues of the compound. The desired in vitro potency of the inhibitor was such that the compound is useful as a therapeutic agent, i.e. in the nanomolar or micromolar range.

Inhibition of the PKB in vitro was measured by scintillation counting, which involves the incorporation of radioactive phosphate onto a specific substrate which is immobilized onto a filter paper at the end of the assay. The assay was performed in the absence and presence of specific and known inhibitors of PKB (as controls), and the amount of incorporated radioactivity was compared.

The baseline activity is defined here is the amount of radioactivity incorporated in the absence of inhibitor. The amount of radioactivity incorporated in the presence of an inhibitor is called the 'sample activity', and the percent inhibition is expressed by the following formula:

$$\% \text{ inhibition} = 100 - (\text{sample activity/baseline activity} \ast 100)$$

and is usually expressed in conjunction with the compound concentration. By using a range of inhibitor concentrations, the concentration at which enzymatic activity is reduced by 50% of an inhibitor is estimated (the "IC$_{50}$"). The IC$_{50}$ of various compounds against a particular target can be compared, where a lower IC$_{50}$ indicates a more potent compound.

Materials and Methods

Inhibition Assay: Representative compounds of the invention were lyophilized and stored at minus 20° C. Stock solutions were made by weighing out the compounds and dissolving them in dimethyl sulfoxide (DMSO) to a standard concentration, usually 20 mM, and stored at minus 20° C., or more preferably, prepared immediately before testing. The compounds were diluted to a starting intermediate concentration of 250 μM in 1% DMSO, then serially diluted across a row of a 96 well plate using serial two-fold dilution steps. Diluted 100% DMSO was used as a negative control.

In each well of the Costar serocluster plate, the following volumes of solutions were added:

5 μl diluted compound
  10 μl enzyme preparation
  5 μl substrate solution
  5 μl assay ATP before incubating for 15 min at room temperature.

From each well, 10 μl of reaction mix was spotted onto 96-well Millipore Multiscreen-PH opaque plates with immobilized P81 phosphocellulose membranes and washed 2 times for 10 min in 1% phosphoric acid. The plates were dried for at 40° C. for 30 min and the substrate phosphate complexes were measured by scintillation counting. The degree of inhibition by compounds was recorded and used for synthetic planning. Results shown in Table 1.

PKB used in enzyme assay: The target kinase is a full-length recombinant bovine protein, alpha form, and was prepared by Dr. Jun Yan of Kinetek Pharmaceuticals, Inc., Vancouver. PKB alpha may also be purchased from Stress-Gen Biotechnologies, Corp., in Victoria, Canada.

TABLE 1
| Code | Product | MW | IC$_{50}$ in μm | Cell Proliferation in A459 IC$_{50}$ in nm |
| --- | --- | --- | --- | --- |
| KP-17483 | 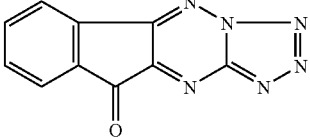 | 224.18 | 15 | >10$^4$ |
| KP-23172 | 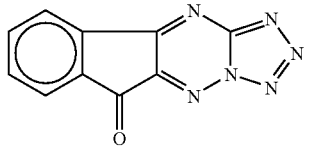 | 224.18 | 15 | 80 |
| KP-23172-001 | 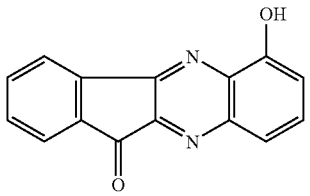 | 248.24 | >10$^2$ | >10$^4$ |
| KP-23172-002 | 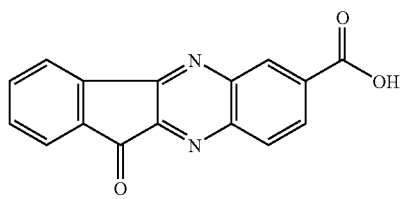 | 276.25 | >10$^2$ | >10$^4$ |
| KP-23172-003 | 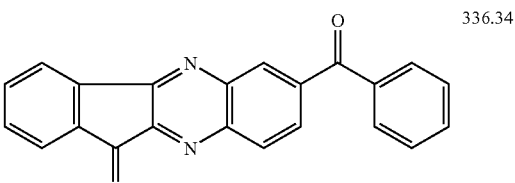 | 336.34 | >10$^2$ | >10$^4$ |
| KP-23172-004 | 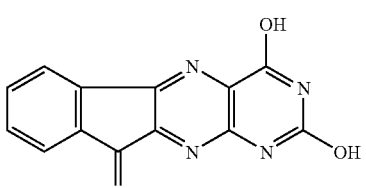 | 266.21 | >10$^2$ | >10$^4$ |
| KP-23172-005 | 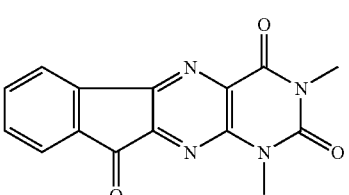 | 294.26 | >10$^2$ | >10$^4$ |
| KP-23172-006 | 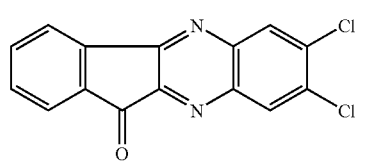 | 301.13 | >10$^2$ | >10$^4$ |

TABLE 1-continued

| Code | Product | MW | IC$_{50}$ in μm | Cell Proliferation in A459 IC$_{50}$ in nm |
|---|---|---|---|---|
| KP-23172-007 | | 260.29 | >10$^2$ | >10$^4$ |
| KP-23172-008 | | 210.19 | >10$^2$ | >10$^4$ |
| KP-23172-009 | | 250.21 | >10$^2$ | >10$^4$ |
| KP-23172-010 | | 250.25 | >10$^2$ | N/a |
| KP-23172-011 | | 224.22 | >10$^2$ | N/a |
| KP-23172-012 | | 248.28 | >10$^2$ | N/a |
| KP-23172-013 | | 260.33 | >10$^2$ | N/a |
| KP-23172-014 | | 150.14 | >10$^2$ | >10$^4$ |
| KP-23172-015 | | 236.27 | >10$^2$ | >10$^4$ |

TABLE 1-continued
| Code | Product | MW | IC$_{50}$ in μm | Cell Proliferation in A459 IC$_{50}$ in nm |
|---|---|---|---|---|
| KP-23172-016 | 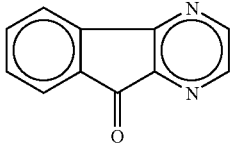 | 182.18 | >10$^2$ | N/a |
| KP-23172-017 | 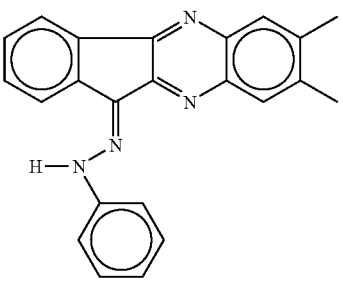 | 350.42 | >10$^2$ | N/a |
| KP-23172-018 | 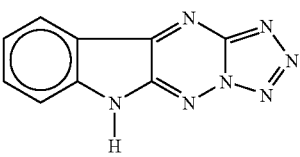 | 211.18 | >10$^2$ | >10$^4$* |
| KP-23172-019 | 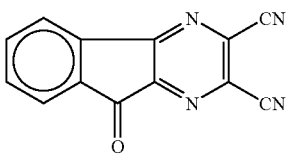 | 232.2 | >10$^2$ | >10$^4$* |
| KP-23172-020 | 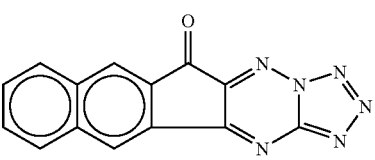 | 274.24 | >10$^2$ | 100 |
| KP-23172-021 | 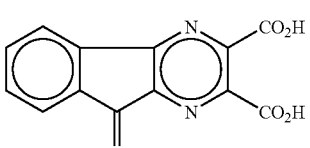 | 270.2 | >10$^2$ | >10$^4$ |
| KP-23172-022 | 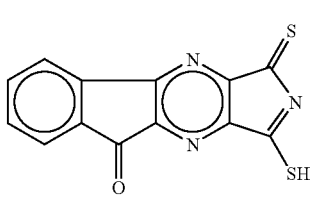 | 283.32 | >10$^2$ | 5 × 10$^3$* |
| KP-23172-023 | 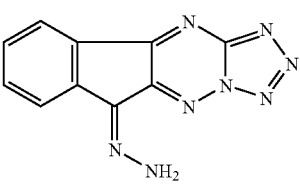 | 238.21 | >10$^2$ | 5 × 10$^2$ |

TABLE 1-continued

| Code | Product | MW | IC$_{50}$ in μm | Cell Proliferation in A459 IC$_{50}$ in nm |
|---|---|---|---|---|
| KP-23172-024 | | 314.3 | >10$^2$ | >10$^4$ |
| KP-23172-025 | | 327.38 | >10$^2$ | N/a |
| KP-23172-026 | | 282.3 | >10$^2$ | N/a |
| KP-23172-027 | | 291.23 | >10$^2$ | 5 × 10$^2$ |
| KP-23172-028 | | 246.26 | >10$^2$ | >10$^4$ |
| KP-23172-029 | | 246.26 | >10$^2$ | >10$^4$ |
| KP-23172-030 | | 254.20 | 20 | 46 |

TABLE 1-continued

| Code | Product | MW | IC$_{50}$ in μm | Cell Proliferation in A459 IC$_{50}$ in nm |
|---|---|---|---|---|
| KP-23172-31 | 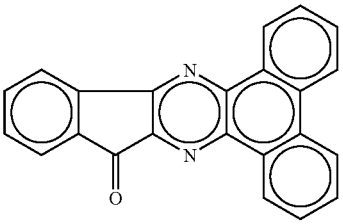 | 332.36 | >10$^2$ | N/a |

*Tested in U7 cells, not A459. Results are expected to be similar between the cell lines.

Example 15

KP-17483 and KP-23172 as Anti-Proliferative Compounds

Material and Methods

Cell lines A-549 (human lung carcinoma), B16-F1 (murine melanoma), B16-F10 (murine melanoma), DU-145 (human pancreatic carcinoma), LS-180 (human colon carcinoma), PC3 (human prostate carcinoma), SKOV-3 (human ovarian carcinoma), U-87 (human glioma), and NIH-3T3 (murine embryonic fibroblasts) were all cultured in DMEM supplemented with 10% fetal bovine serum. M3 murine melanoma cells were cultured in DMEM/F12 1:1, and HT-29 human colon carcinoma and LL2 Lewis Lung human lung carcinoma were cultured in RPMI1640. All the foregoing cell lines were obtained from ATCC.

The human breast carcinoma MDA-MB-435 cell line was obtained from MD Anderson Cancer Center, and cultured in alpha-MEM media supplemented with 10% Fetal Bovine Serum. Cells were maintained in T150 tissue culture flasks, and grown at 37° C. in a humidified 5% $CO_2$ incubator.

All cells were passaged regularly using 0.25% Trypsin-EDTA in order to maintain cells at exponential growth for various experiments. LS 180 cells were passaged without trypsin and were physically scraped off the culture flasks.

In vitro [$^3$H] thymidine uptake assay. Proliferation can be measured by quantifying the amount of [$^3$H] thymidine uptake into cells using a β-counter, and therefore is a well-established diagnostic tool to measure DNA synthesis within the cells. Following passage, a hemacytometer was used to accurately perform the necessary dilutions to obtain the desired concentration of 3.3×10$^4$ cells/mL. 90 μL of this dilution was pipetted into each 96 well culture plate for a final cell density of 3×10$^3$ cells/well. The cells were allowed to adhere to the plates via incubation at 37° C. in 5% $CO_2$ for 12–14 hours. Adequate amounts of [$^3$H] thymidine were added to cell culture media for a final activity of 1 uCi/10 μL, and this media was used to prepare test compounds at 10 times the final desired concentration. Then, 10 μL of the compound was added to the pre-existing 90 μL per well, and incubated further at 37° C. in 5% $CO_2$ for 20 hours. To measure thymidine incorporation, cells were fixed onto the culture wells by slowly adding ¼$^{th}$ volume of cold 50% TCA into each well (25 μL to each well) and incubated for 1–2 hours at 4° C. Wells were washed 5 times with tap water to remove any free [$^3$H] thymidine in the media, and air-dried completely at room temperature. Then, 100 μL of scintillation fluid was added to each well and the activity counted using a Wallac Microbeta Counter.

Results

Concentrations of 10 μM of compound were found to completely inhibit proliferation in all cell lines (data shown in Table 2). For sensitive cell lines, e.g. B16F1, DU145, and U-87, concentrations of 400 nM and higher were completely inhibitory, and IC$_{50}$ values were less than 100 nM. The IC$_{50}$ values for less sensitive cell lines like HT-29, LL2, and PC-3 were in the 200 to 750 nM range. As an indication of therapeutic potential for these compounds, a non-tumorigenic cell line was also tested and was found to have an IC$_{50}$ of 150 to 200 nM. This indicates that this is less sensitive to the compounds than the "tumorigenic" cell lines like B16-F1, DU-145, and U-87. The dose response to KP-23172 is shown in FIG. 1.

TABLE 2

KP-17483 and KP-23172 Effect On Cellular Proliferation

| Cell Line | Cell Proliferation Effects (IC$_{50}$ (nM)) | |
|---|---|---|
| | KP-17483 | KP-23172 |
| A549 | Not done | 80 |
| B16F1 | 80 | 60 |
| B16F10 | 750 | 400 |
| DU145 | 50 | 50 |
| HT29 | 500 | 200 |
| LL2 | 750 | 400 |
| M3 | 30 | 25 |
| PC3 | 250 | 250 |
| SKOV3 | 300 | 200 |
| U87 | 50 | 50 |
| NIH3T3 | 200 | 150 |
| LS180 | Not done | 80 |
| MDA435 | Not done | 60 |

Example 16

DNA Fragmentation Apoptosis Assay (TUNEL Assay)

Apoptosis or programmed cell death is an active process characterized by cell shrinkage, plasma and mitochondrial membrane changes, activation of apoptosis related enzymes such as the caspases, chromatin condensation, formation of membrane-enclosed vesicles (apoptotic bodies), and DNA fragmentation. One widely accepted measure of nicking and fragmentation of chromosomal DNA is the TUNEL assay.

The TUNEL technique (TUNEL is an acronym standing for: "terminal deoxynucleotidyl transferase dUTP nick end labeling") employs terminal deoxynucleotidyl transferase to label the 3'-hydroxy ends of DNA resulting from single stranded nicks and double stranded breaks in DNA associated with later stages of apoptosis. The assay was originally developed using biotin-labeled dUTP (Gavrieli et al. (1992) J. Cell Biol. 119:493–501) but other means of deoxynucleotide labeling range from biotin, digoxigenin, and FITC to $^{32}$P and $^3$H. Because the assay is able to detect DNA nicking as well as fragmentation, and because of the increased sensitivity of the label, the TUNEL assay is inherently more sensitive than the previous DNA fragmentation assays.

Methods and Materials

Cultured cells were seeded into 96 well tissue culture plates to 80% confluency and then treated with inhibitor compound for 24 hours. Cells were then fixed in-situ with 4% paraformaldehyde. TUNEL labeling with α32P-dATP and terminal transferase was carried out directly in the 96 well plates following a procedure adapted from Sgonc, R. et. al. 1994. Trends in Genetics. 10:41–42.

Figure 2:
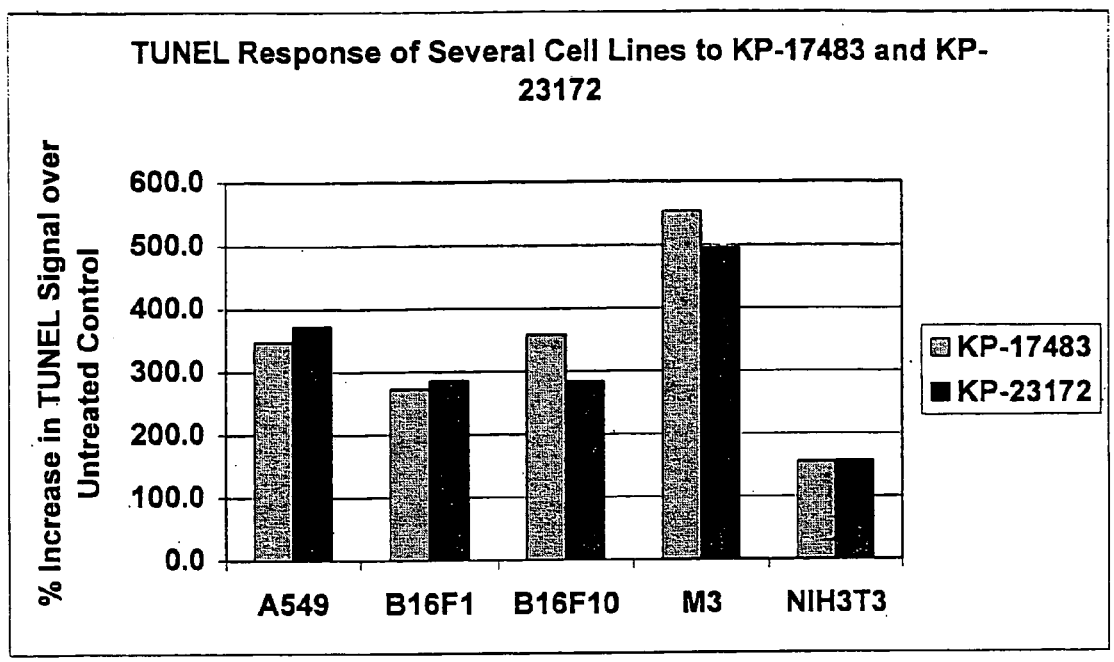
FIG. 2 shows a graph of the response of several cell lines to KP-17483 and KP-23172 at a concentration of 2 μM compound as measured by the TUNEL apoptosis assay.
Figure 3:
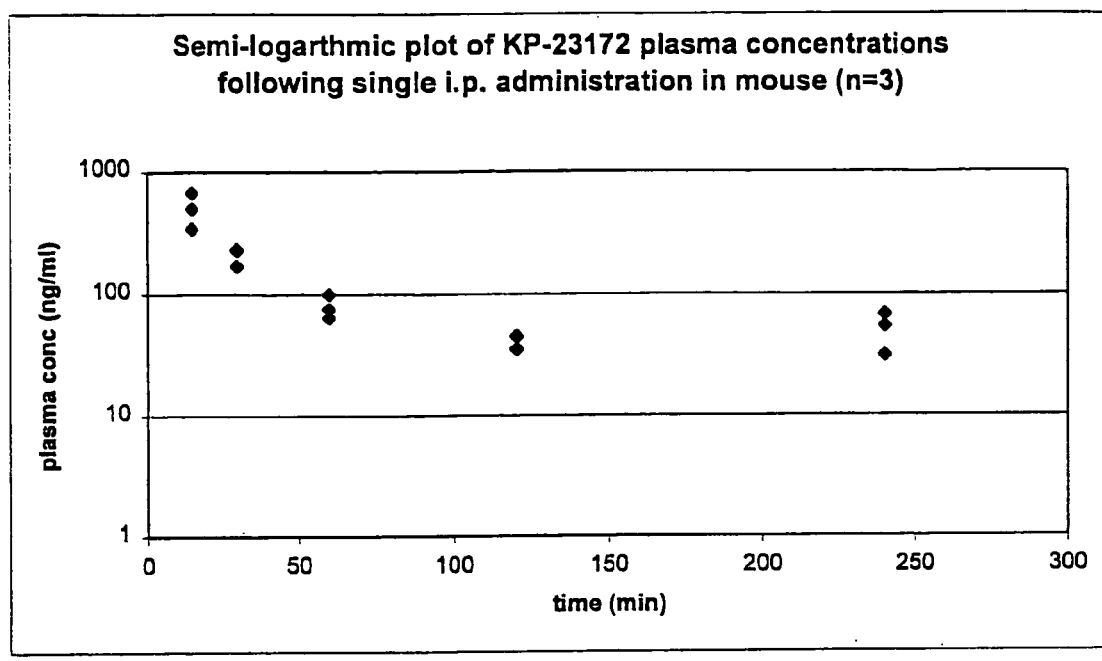
FIG. 3 shows the semi-logarithmic plot of KP-23172 plasma concentrations in mice following a single intraperitoneal administration.

Data is shown in FIG. 2.

Example 17

Assessment of Effects on Cell Viability In Vivo Xenograft Model

Mice were inoculated subcutaenously in the rear flank with Lewis Lung tumour cell line (LS180) and then injected daily with KP-23172 i.p. Tumour measurements were taken daily.

Figure 4:
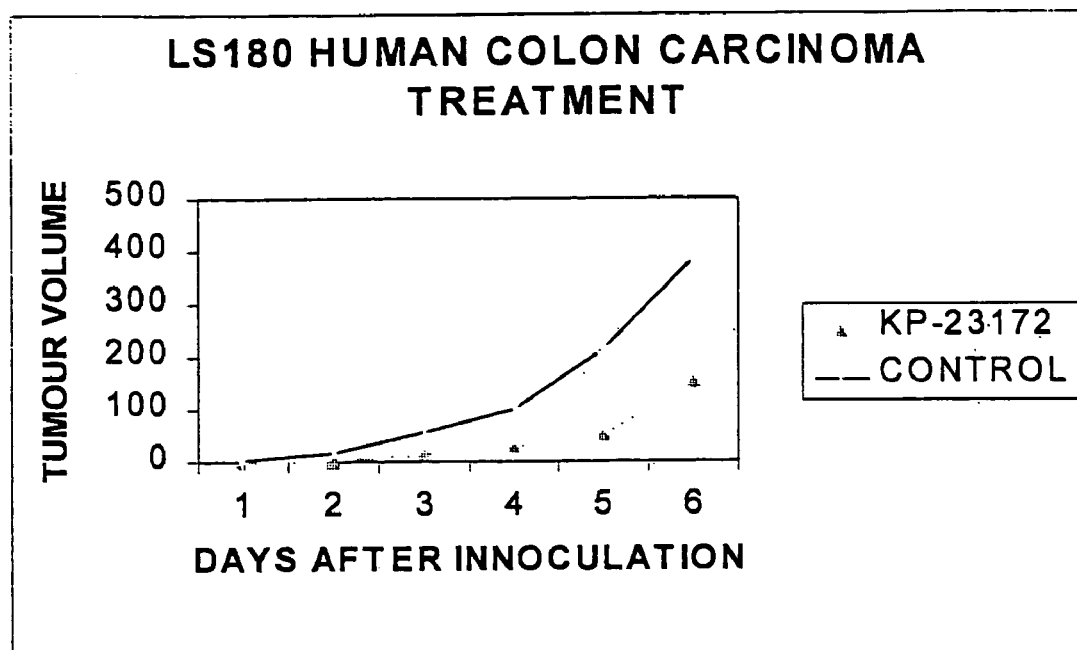
FIG. 4 is a graph depicting the growth of tumors in the presence of KP-23172.

A group of 8 athymic (Rag2M) female mice were used as a murine allograft model for the test compound, which was administered in DMSO. 8 control mice received no test compound. Mice were inoculated with tumour cells subcutaneously in the rear flank and then injected with test compound daily intraperitoneally. Tumors were measured and the size calculated, with the objective being a reduction in tumor growth compared to controls. In this study, the control mice had a tumour take rate of 100% by day 15 while mice treated with the 2.5 mg/kg of KP-23172 test compound had a tumor take rate of 62.5% at the same time point, demonstrating a reduction in tumor growth associated with the compound. Results are illustrated in FIG. 4.

Example 18

Formulation and Stability

A non-DMSO containing formulation was required for in vivo testing of the compounds as animals injected with DMSO control showed DMSO-related effects which would impede analysis of test compounds.

Solubility of KP-23172 was studied in various percent solutions of hydroxypropyl-B-cyclodextrin in water. KP-23172 was soluble in cyclodextrin solutions in the absence of propylene glycol. Solubility was linear up to 30% cyclodextrin. The intrinsic water solubility was 77 ug/mL, solubility in 30% cyclodextrin was 728 ug/mL and the 1:1 binding constant for the KP-23172: cyclodextrin inclusion complex was 474. For comparison, miconazole has been reported in the literature to have a 1:1 binding constant of 363.

A 4-week stability study was undertaken with KP-23172 formulated at 0.1 and 0.2 mg/ml in 10% propylene glycol, 20% hydroxypropyl-B-cyclodextrin in water. Aliquots of 0.5 mL were stored at room temperature in the light, room temperature in the dark, at 4° C. and at −20° C. (both in the dark) in sealed tubes under a head of $N_2$.

Figure 5:
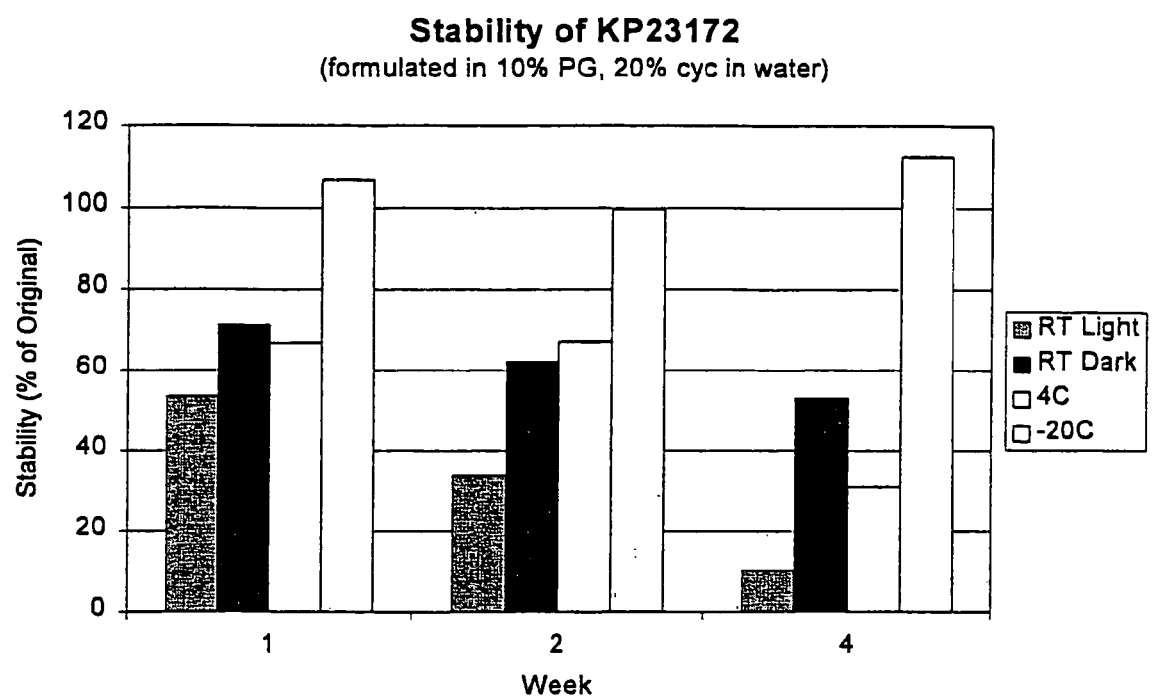
FIG. 5 shows the results of a 4 week stability study performed on a formulation of KP-23172 in 10% propylene glycol and 20% hydroxypropyl-B-cyclodextrin in deoxygenated water under a head of $N_2$ gas.

The samples were tested in a cell based assay comparing the activity of the older samples to freshly prepared samples. The samples were also analyzed by HPLC and the data are presented in FIG. 5. Good correlation was observed between HPLC analyses of stability and activity of the solutions in cell-based assays.

Example 19

LC/MS/MS Determination of KP-23172 in Mouse Plasma Study Samples

A pharmacokinetics (PK) study was performed on KP-23172 formulated in 20% propylene glycol and 20% hydroxypropyl-B-cyclodextrin, administered intraperitoneally (i.p.) at 2 mg/kg. Plasma samples obtained at various time points were sent to BRI Biopharmaceutical Research Inc., Burnaby, BC, Canada for analysis by Liquid Chromatography/Mass Spectroscopy (LC/MS).

Electrospray LC/MS/MS data was acquired in the multiple-reaction-monitoring mode (MRM) in which m/z 225.00>114.20 was monitored for KP-23172 as its $[M+H]^+$ transition to an ion fragment of m/z 114.2. A mass ion transition of m/z 300.00>165.10 was being monitored for codeine as an internal standard. MRM chromatograms of mouse plasma standard curve samples spiked with 1 and 5000 ng/ml were performed as controls.

Plasma calibration standard curves were established based on 1/y linear regression of plasma concentrations of KP-23172 against peak area ratio to the internal standard. The calculated KP-23172 plasma concentrations were based on the assay of 0.05 ml of plasma volume used in the assay and reported as ng/ml concentration.

A summary of the KP-23172 plasma concentrations observed in 20 samples from 4 mice is presented in FIG. 2 as a semi-logarithmic plot of the plasma concentrations against blood collection times.

In summary, these data show that KP-23172 in a 20% propylene glycol –20% hydroxypropyl cyclodextrin formulation administered in a single dose of 2 mg/kg i.p. is absorbed and enters the bloodstream of the animal, giving blood levels of about 500 ng/ml at 15 min, 100 ng/ml at 60 min, and 50 ng/ml at about 120 min. The Pharmacokinetetics is biphasic, with a half-life of about ½ hour when blood levels are higher than 100 ng/ml.

Example 20

The Effect of KP-17483 on PKB Activity

A time course kinase assay was performed on U87 cells where 5 iM KP-23172 significantly decreased levels of the kinase after 60 minutes. The compound was added to culture at mid-logarithmic growth which were harvested at specific time intervals.

In one assay, PC3 cells are grown and incubated with differing concentrations of test compounds, then then cell lysate is Western blotted with an antibody such as phospho AKT-ser 473 from (New England Biolabs). Resultant bands are observed using densitometric analysis.

In other experiments, specially prepared human tissue samples are used. The cells are still metabolizing. Test compounds of the invention are incubated with the tissues overnight. The tissues are then stained immunohistochemically and a reduction in PKB levels is observed.

One antibody known as Kinetek PHB-PH is prepared in house. This antibody is used in conjunction with AKT-Ser 473 to confirm the concentration of PKB protein while the AKT-Ser473 is used to determine phosphorylation changes.

In preparation for this assay, each cell line was seeded at a density of 3 times 1,000,000 cells per plate onto 150 mm culture dishes and allowed to establish o/n at 37 deg C. A confluency of 50–60% was obtained to ensure maximal drug penetration into each cell. Once the cells were adherent to the culture plates, there were treated with PKB inhibitor KP-23172 for a final conc. of 5 uM. Each culture plate was lysed on ice at specific time intervals using 1% NP-40 lysis buffer containing various protease inhibitors; 10 ug/uL aprotinin, 10 ug/ul leupeptin, 1 ug/ul pepstatin, 1 M beta-glycerophosphate and 100 mM PMSF. The resulting lysates were centrifuged at 15K×g at 4 deg C. for 5 min and then assayed for its protein conc. using Bradford's Reagent and absorbance measurements at 595 nm. Equal amounts of protein were transferred to a new centrifuge tube and treated with anti-PKB-PH antibody (Kinetek #XXP-021), anti-PK-Balpha antibody (Signal Transduction #67220), or anti-PKB gamma antibody (UBI 306-607) and incubated end over end at 4 deg C. Each sample was then centrifuged at 14K×g for 2 min at 4 deg C. and the s/n aspirated off. Beads were thoroughly washed twice with lysis buffer, then with Assay Dilution Buffer. When any unbound proteins have been completely washed away from the beads, 30 uL of ADB was added along with 10 uL of PDB substrate. Tubes were immediately incubated in 30 deg. C. water baths after the kinase reaction was allowed to commence with the addition of 10 uL assay (gamma32P)ATP. After the 20 min incubation period, the s/n was spotted onto p81 cation exchange chromatography paper and any unbound ATP washed with 1% phosphoric acid. to count the amt of substrate phosphorylation, hence kinase activity, the substrate bound filter papers was allowed to air dry for 15 min and placed in scintillation vials along with 0.5 mL of liquid scintillation cocktail. All vials were counted for one minute in the scintillation counter.

KP-23172 on PKB Activity

To determine the potency of KP-23172, U87 cells were plated onto 150 mm petri plates and treated with 5 uM KP-23172. After incubation at 37 deg C. under 5% CO2 for the specified time, cells were lysed and the supernatant extracted for kinase analysis. All samples were immunoprecipitated with PKB/PH specific antibody and kinase activity. measured using a short amino acid peptide as the substrate. After 15 min, the PKB activity was 80.4% of control, then down to 23.8% after 30 min. Finally after 60 min, the total PKB activity had decreased to 38.5% of control, indicated that KP-23172 had substantial impact on PKB activity. Background was about 15% of control.

Several isoforms of PKB have been shown to be upregulated in certain tumor models including breast and prostate cancers. A kinase assay in cells was also performed using anti PKB alpha and gamma antibodies in order to determine any inhibition of the isoforms by KP-23172. U87 cells were treated with 5 uM compound, lysed, and the resulting supernatant was analyzed for any changed in PKB activity. Similar effects were observed between the alpha and gamma isoforms, resulting in a reduction of activity to 29.6% and 18.3% after 60 min, respectively. Anti PKB alpha and gamma antibodies may have some cross reactivity to other isoforms.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of inhibiting tumor growth, the method comprising:
   administering an effective dose of a compound having a formula selected from the group consisting of

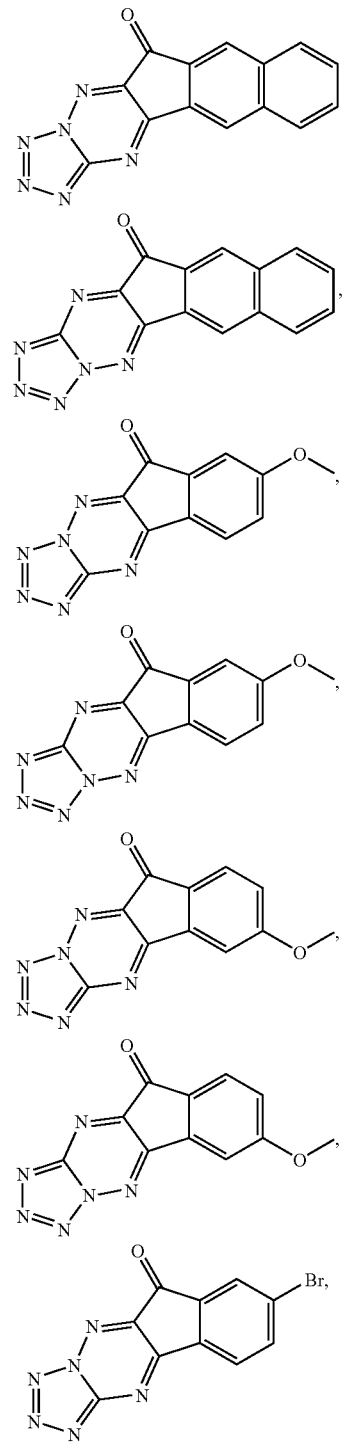

-continued
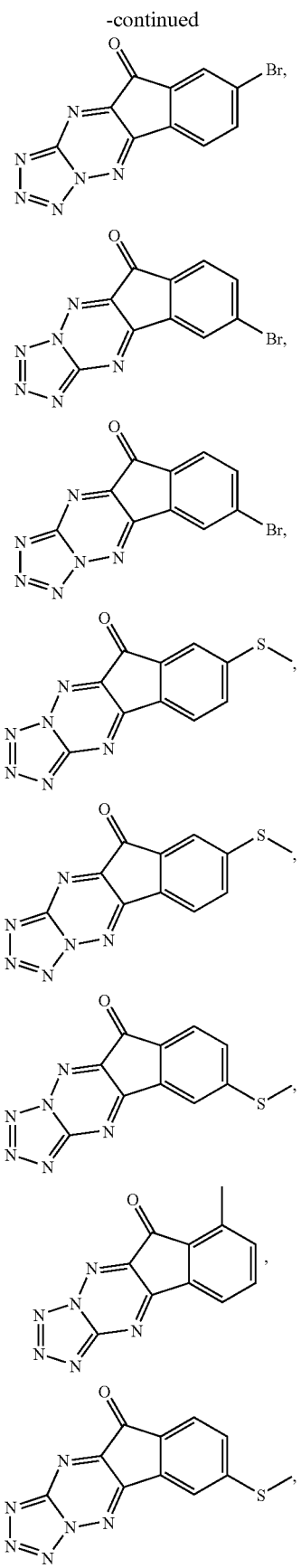
-continued
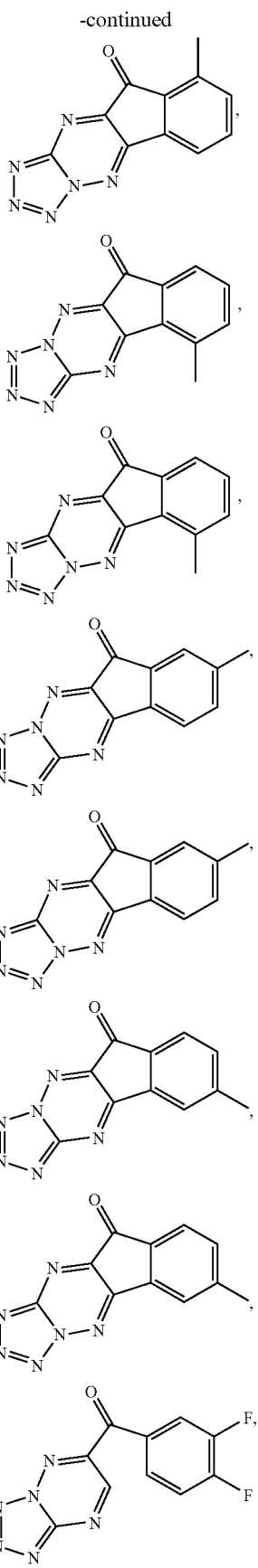

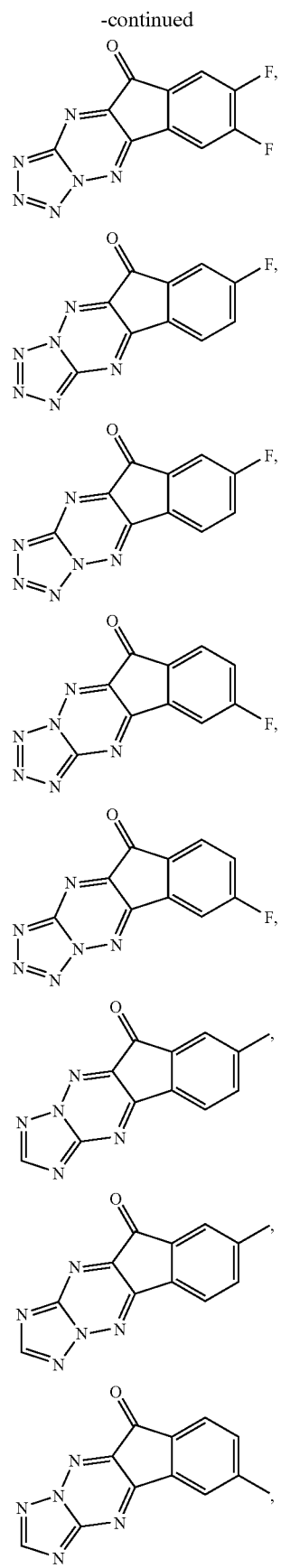
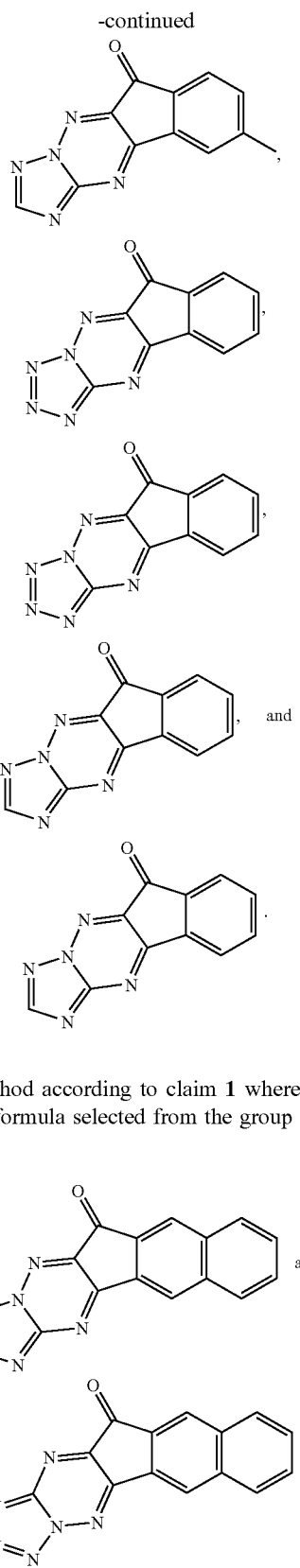
2. The method according to claim 1 wherein said compound has a formula selected from the group consisting of
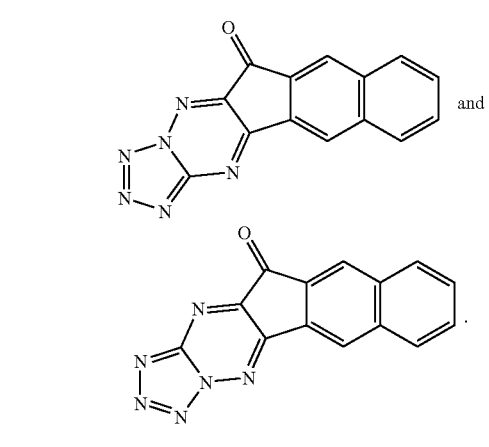
3. The method according to claim 1 wherein said compound has a formula selected from the group consisting of

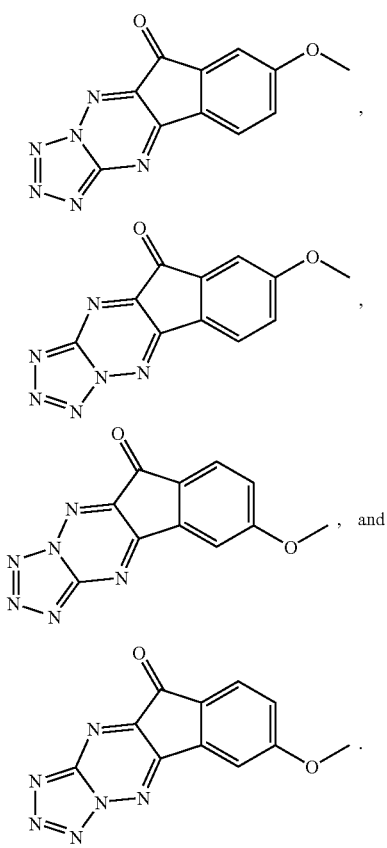
4. The method according to claim 1 wherein said compound has a formula selected from the group consisting of
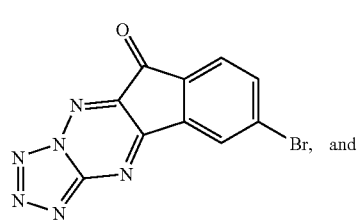
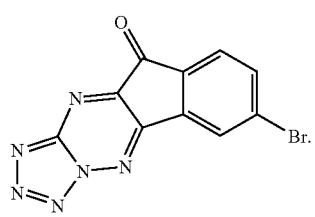
5. The method according to claim 1 wherein said compound has a formula selected from the group consisting of
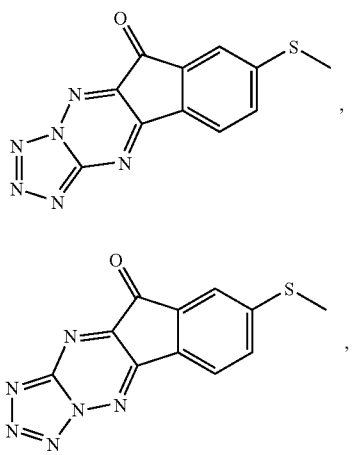
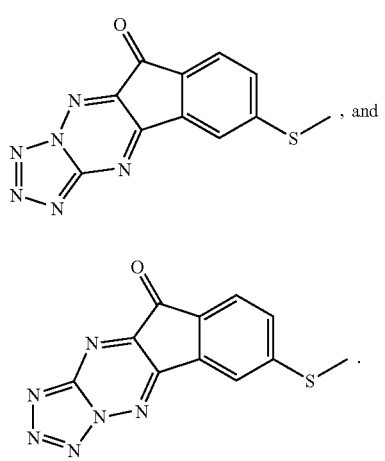
6. The method according to claim 1 wherein said compound from the group consisting of -continued

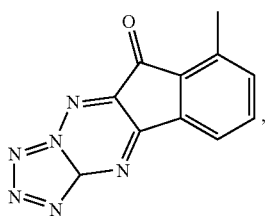

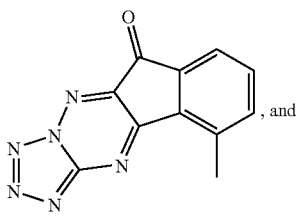, and

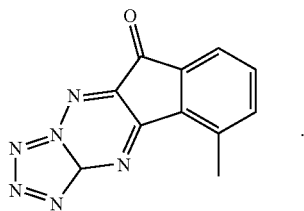.

7. The method according to claim 1 wherein said compound from the group consisting of

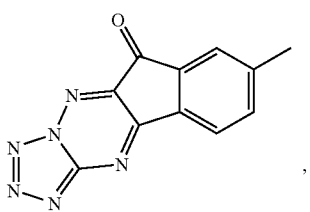,

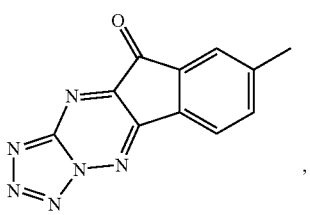,

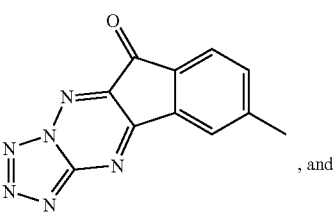, and

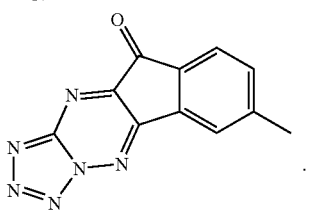.

8. The method according to claim 1 wherein said compound has a formula selected from the group consisting of

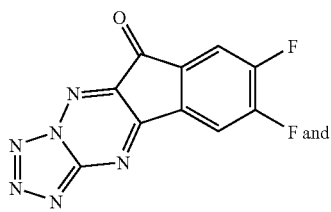 and

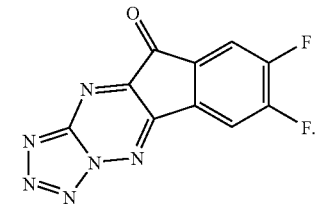.

9. The method according to claim 1 wherein said compound has a formula selected from the group consisting of

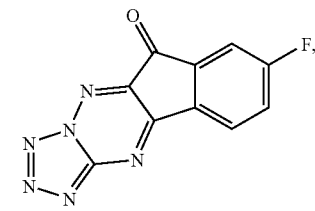,

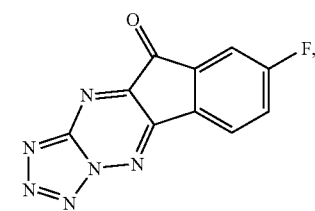,

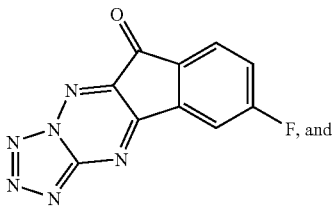, and

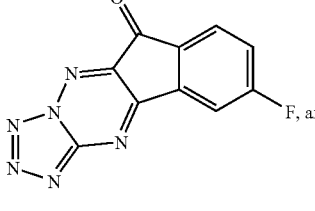.

10. The method according to claim 1 wherein said compound has a formula selected from the group consisting of

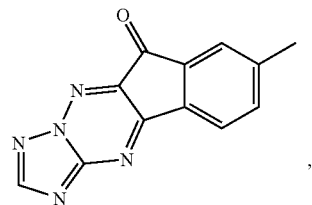
,
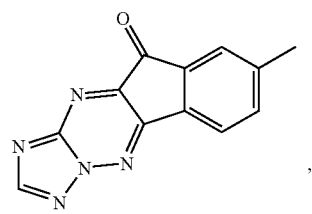
,
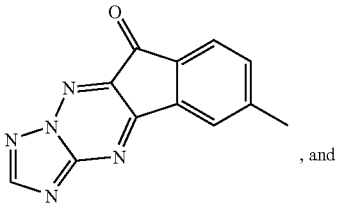
, and
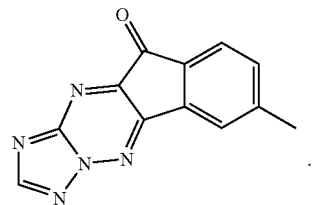
.
11. The method according to claim 1 wherein said compound has a formula selected from the group consisting of
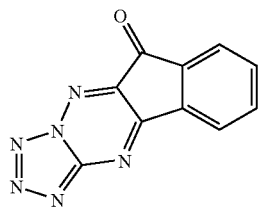
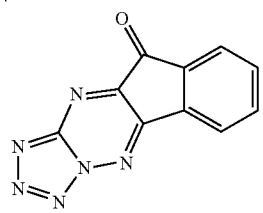
and
12. The method according to claim 1 wherein said compound has a formula selected from the group consisting of
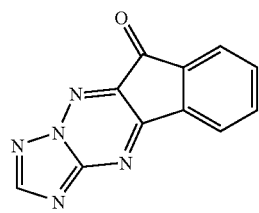
and
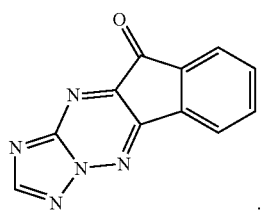
.
* * * * *